(12) United States Patent
Thome et al.

(10) Patent No.: US 12,128,092 B2
(45) Date of Patent: Oct. 29, 2024

(54) LYOPHILIZED FACTOR IX FORMULATIONS

(71) Applicant: Bioverativ Therapeutics Inc., Waltham, MA (US)

(72) Inventors: Brian M. Thome, Boston, MA (US); Cherie Parkhurst-Lang, Londonderry, NH (US); Brandon W. Leveille, Berwick, MA (US)

(73) Assignee: BIOVERATIV THERAPEUTICS INC., Waltham, MA (US)

( * ) Notice: Subject to any disclaimer, the term of this patent is extended or adjusted under 35 U.S.C. 154(b) by 616 days.

(21) Appl. No.: 16/995,173

(22) Filed: Aug. 17, 2020

(65) Prior Publication Data

US 2021/0069307 A1 Mar. 11, 2021

Related U.S. Application Data

(62) Division of application No. 15/128,951, filed as application No. PCT/US2015/022141 on Mar. 24, 2015, now Pat. No. 10,772,942.

(60) Provisional application No. 61/969,801, filed on Mar. 24, 2014.

(51) Int. Cl.

| A61K 38/36 | (2006.01) |
| A61K 9/00 | (2006.01) |
| A61K 9/19 | (2006.01) |
| A61K 38/48 | (2006.01) |
| A61K 47/18 | (2017.01) |
| A61K 47/22 | (2006.01) |
| A61K 47/26 | (2006.01) |
| F26B 5/06 | (2006.01) |

(52) U.S. Cl.
CPC ........ *A61K 38/4846* (2013.01); *A61K 9/0019* (2013.01); *A61K 9/19* (2013.01); *A61K 47/183* (2013.01); *A61K 47/22* (2013.01); *A61K 47/26* (2013.01); *C12Y 304/21022* (2013.01); *F26B 5/06* (2013.01)

(58) Field of Classification Search
None
See application file for complete search history.

(56) References Cited

U.S. PATENT DOCUMENTS

| 5,712,122 | A | 1/1998 | Boime et al. |
| 5,733,873 | A | 3/1998 | Oesterberg et al. |
| 6,685,940 | B2 | 2/2004 | Andya et al. |
| 6,686,179 | B2 | 2/2004 | Fleer et al. |
| 7,592,010 | B2 | 9/2009 | Rosen et al. |
| 7,632,921 | B2 | 12/2009 | Pan et al. |
| 7,790,415 | B2 | 9/2010 | Gillies et al. |
| 7,862,820 | B2 * | 1/2011 | Peters .................. C07K 14/755 424/179.1 |
| 8,015,841 | B2 | 9/2011 | Cheng |
| 8,048,848 | B2 | 11/2011 | Fares et al. |
| 8,367,805 | B2 | 2/2013 | Chamberlain et al. |
| 8,563,521 | B2 | 10/2013 | Skerra et al. |
| 10,588,949 | B2 * | 3/2020 | Brader .................. A61K 47/02 |
| 10,772,942 | B2 * | 9/2020 | Thome ................ A61K 9/0019 |
| 2001/0031721 | A1 | 10/2001 | Webb et al. |
| 2001/0038859 | A1 | 11/2001 | Maskiewicz et al. |
| 2005/0226893 | A1 | 10/2005 | Juneau et al. |
| 2007/0021338 | A1 | 1/2007 | Hansen et al. |
| 2007/0135343 | A1 * | 6/2007 | Webb ..................... A61K 47/02 514/14.2 |
| 2007/0259402 | A1 | 11/2007 | Peters et al. |
| 2008/0060379 | A1 | 3/2008 | Cheng |
| 2009/0087411 | A1 | 4/2009 | Fares et al. |
| 2009/0163699 | A1 | 6/2009 | Chamberlain et al. |
| 2009/0264627 | A1 | 10/2009 | Gillies et al. |
| 2010/0041870 | A1 | 2/2010 | Tchessalov et al. |
| 2010/0292130 | A1 | 11/2010 | Skerra et al. |
| 2011/0236412 | A1 | 9/2011 | Drew |
| 2012/0116054 | A1 | 5/2012 | Krishnan et al. |
| 2012/0121580 | A1 * | 5/2012 | Bhambhani ...... A61K 39/39591 424/130.1 |
| 2016/0000888 | A1 | 1/2016 | Brader |
| 2017/0173122 | A1 | 6/2017 | Thome et al. |

FOREIGN PATENT DOCUMENTS

| CL | 2015002719 A1 | 4/2016 |
| DE | 4405426 A1 | 8/1995 |
| EP | 0154316 B1 | 9/1989 |
| EP | 0401384 B1 | 3/1996 |
| EP | 0758248 A1 | 2/1997 |
| EP | 1219298 A1 | 7/2002 |
| EP | 2222315 A1 | 9/2010 |
| EP | 2173890 B1 | 3/2011 |
| EP | 3123090 A1 | 2/2017 |

(Continued)

OTHER PUBLICATIONS

Warne, N.W., Eur J Pharm Biopharm. Jun. 2011;78(2):208-12. doi: 10.1016/j.ejpb.2011.03.004. Epub Mar. 23, 2011.*

Andersson, L.O., et al., "Purification and Characterization of Human Factor IX," Thrombosis Research 7(3):451-459, Pergamon Press, Inc., United States (Sep. 1975).

(Continued)

*Primary Examiner* — Michael Szperka

(74) *Attorney, Agent, or Firm* — LATHROP GPM LLP; James H. Velema, Esq.

(57) ABSTRACT

The present invention provides, among other things, pre-lyophilization formulations, reconstituted formulations, and lyophilate powder compositions comprising a Factor IX (FIX) polypeptide. The present invention also provides lyophilization methods for producing lyophilate powder comprising a FIX polypeptide.

36 Claims, 5 Drawing Sheets

Specification includes a Sequence Listing.

(56) References Cited

FOREIGN PATENT DOCUMENTS

| | | |
|---|---|---|
| JP | H 07-501560 A | 2/1995 |
| JP | H 09-511495 A | 11/1997 |
| JP | 2001-151694 A | 6/2001 |
| JP | 2002-513390 A | 5/2002 |
| JP | 2005-060378 A | 3/2005 |
| JP | 2006-257099 A | 9/2006 |
| JP | 2007-504267 A | 3/2007 |
| JP | 2007-224052 A | 9/2007 |
| JP | 2009-513705 A | 4/2009 |
| JP | 2009-532394 A | 9/2009 |
| JP | 2010-502932 A | 1/2010 |
| JP | 2011-507919 A | 3/2011 |
| JP | 2011-530524 A | 12/2011 |
| JP | 2012-530721 A | 12/2012 |
| JP | 2013-534426 A | 9/2013 |
| JP | 2014-051503 A | 3/2014 |
| JP | 2015-521589 A | 7/2015 |
| JP | 2016-519670 A | 7/2016 |
| WO | WO 1992/016221 A1 | 10/1992 |
| WO | WO 1994/007510 A1 | 4/1994 |
| WO | WO 1995/022347 A1 | 8/1995 |
| WO | WO 1995/028954 A1 | 11/1995 |
| WO | WO 1995/034326 A1 | 12/1995 |
| WO | WO 1997/026909 A1 | 7/1997 |
| WO | WO 1998/016250 A1 | 4/1998 |
| WO | WO 2002/040544 A3 | 10/2002 |
| WO | WO 2003/020764 A2 | 3/2003 |
| WO | WO 2004/101740 A2 | 11/2004 |
| WO | WO 2005/025499 A2 | 3/2005 |
| WO | WO 2006/029467 A1 | 3/2006 |
| WO | WO 2006/065861 A2 | 6/2006 |
| WO | WO 2006/074199 A1 | 7/2006 |
| WO | WO 2007/053533 A2 | 5/2007 |
| WO | WO 2007/112005 A2 | 10/2007 |
| WO | WO 2007/149406 A2 | 12/2007 |
| WO | WO 2007/112757 A2 | 2/2008 |
| WO | WO 2008/118507 A2 | 10/2008 |
| WO | WO 2008/155134 A1 | 12/2008 |
| WO | WO 2009/051717 A2 | 4/2009 |
| WO | WO 2009/083187 A1 | 7/2009 |
| WO | WO 2009/130198 A2 | 10/2009 |
| WO | WO 2009/130602 A2 | 10/2009 |
| WO | WO 2009/137254 A2 | 11/2009 |
| WO | WO 2009/140015 A2 | 11/2009 |
| WO | WO 2010/017296 A1 | 2/2010 |
| WO | WO 2010/148337 A1 | 12/2010 |
| WO | WO 2011/017070 A1 | 2/2011 |
| WO | WO-2012006624 A2 * | 1/2012 ............ A61K 38/36 |
| WO | WO 2012/043696 A1 | 4/2012 |
| WO | WO 2012/109429 A2 | 8/2012 |
| WO | WO 2013/185113 A1 | 12/2013 |
| WO | WO 2014/052490 A1 | 4/2014 |
| WO | WO-2014144549 A1 * | 9/2014 ......... A61K 38/4846 |
| WO | WO 2015/148444 A1 | 10/2015 |

OTHER PUBLICATIONS

Armour, K.L., et al., "Recombinant Human IgG Molecules Lacking Fcgamma Receptor I Binding and Monocyte Triggering Activities," European Journal of Immunology 29(8):2613-2624, Wiley-VCH, Germany (Aug. 1999).

Arshad, M.S., "Application of Through-vial Impedance Spectroscopy as a Novel Process Analytical Technology for Freeze Drying," PHD Thesis, De Montfort University, Leicester, Mar. 11, 2014, Retrieved from the Internet: URL:http://hdl.handle.net/2086/10407, on May 25, 2015, pp. 1-255.

Bai, Y., et al., "Recombinant Granulocyte Colony-stimulating Factor-transferrin Fusion Protein as an Oral Myelopoietic Agent," Proceedings of the National Academy of Sciences USA 102(20):7292-7296, National Academy of Sciences, United States (May 2005).

Bioverativ Therapeutics Inc., "Highlights of Prescribing Information, Alprolix", U.S. Food and Drug Administration, 2014, 25 Pages, obtained from url: http://www.fda.govjdownloads/BiologicsBloodVaccines/BloodBloodProducts/ApprovedProducts/LicensedProductsBLAs/FractionatedPlasmaProducts/UCM391049.pdf.

Brandsma, M.E., et al., "Recombinant Human Transferrin: Beyond Iron Binding and Transport," Biotechnology Advances 29(2):230-238, Elsevier, United States (Mar. 2011).

Burmeister, W.P., et al., "Crystal Structure of the Complex of Rat Neonatal Fc Receptor with Fc," Nature 372(6504):379-383, Nature Publishing Group, England (Nov. 1994).

Czajkowsky et al., EMBO Mol Med. Oct. 2012;4(10):1015-28. doi: 10.1002/emmm.201201379. Epub Jul. 26, 2012.

Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (Sep. 2002).

European Search Report for European Patent Application No. 15769411.8, dated Nov. 15, 2017.

Francis, G.E., "Protein Modification and Fusion Proteins," Focus on Growth Factors 3(2):4-10, Mediscript, England (1992).

Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (Dec. 1999).

GenBank, "*Homo sapiens* Transferrin (TF), mRNA," Accession No. XM002793, accessed at https://www.ncbi.nlm.nih.gov/nuccore/XM_002793.7?report=genbank, accessed on Jan. 1, 2018, 2 pages.

Genbank, "*Homo sapiens* transferrin (TF), mRNA," Accession No. XM039845, accessed at https://www.ncbi.nlm.nih.gov/nuccore/XM_039845.1?report=genbank, accessed on Jan. 1, 2018, 2 pages.

Genbank, "*Homo Sapiens* transferrin (TF), mRNA," Accession No. XM039847, accessed at https://www.ncbi.nlm.nih.gov/nuccore/XM_039847.1?report=genbank, accessed on Jan. 1, 2018, 2 pages.

Genbank, "*Homo sapiens* transferrin (TF), transcript variant 1. mRNA," Accession No. NM001063, accessed at https://www.ncbi.nlm.nih.gov/nuccore/NM_001063, accessed on Jan. 1, 2018, 5 pages.

Genbank, "Human transferrin mRNA, complete cds," Accession No. M12530, accessed at https://www.ncbi.nlm.nih.gov/nuccore/339452/, accessed on Jan. 1, 2018, 2 pages.

Genbank, "Transferrin [human, liver, mRNA, 2347 nt]," Accession No. S95936, accessed at https://www.ncbi.nlm.nih.gov/nuccore/595936, accessed on Jan. 1, 2018, 2 pages.

Holt, L.J., et al., "Anti-Serum Albumin Domain Antibodies for Extending the Half-lives of Short Lived Drugs," Protein Engineering, Design and Selection 21(5):283-288, Oxford University Press, England (May 2008).

International Search Report and Written Opinion for PCT International Application No. PCT/US2015/022141, ISA/US, mailed on Jul. 9, 2015.

Johnson et al., "Freeze-Drying Protein Formulations above their Collapse Temperatures: Possible Issues and Concerns", American Pharmaceutical Review, Apr. 1, 2011, 8 pages.

Kabat, E.A., et al., "Sequences of Proteins of Immunological Interest," 5th Edition, U.S. Department of Public Health and Human Services, Public Health Service, National Institutes of Health, Bethesda (1991).

Kim, B.J., et al., "Transferrin Fusion Technology: a Novel Approach to Prolonging Biological Half-life of Insulinotropic Peptides," The Journal of Pharmacology and Experimental Therapeutics 334(3):682-692, American Society for Pharmacology and Experimental Therapeutics, United States (Sep. 2010).

Kraulis, P.J., et al., "The Serum Albumin-binding Domain of Streptococcal Protein G is a Three-helical Bundle: A Heteronuclear NMR Study," FEBS Letters 378(2):190-194, Elsevier Science B.V, Netherlands (Jan. 1996).

Li, H., et al., "The Role of the Transferrin-transferrin-receptor System in Drug Delivery and Targeting," Trends in Pharmacological Sciences 23(5):206-209, Elsevier Science Ltd., England (May 2002).

Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (Feb. 2002).

(56) References Cited

OTHER PUBLICATIONS

Malik, F., et al., "Polyethylene Glycol (PEG)-modified Granulocyte-macrophage Colonystimulating Factor (GM-CSF) with Conserved Biological Activity," Experimental Hematology 20(8):1028-1035, International Society for Experimental Hematology, United States (Sep. 1992).
McCue, et al. (May 2014) "Validation of the manufacturing process used to produce long-acting recombinant factor IX Fc fusion protein", Haemophilia, vol. 20(4) e327-35.
Mei, B., et al., "Rational Design of a Fully active, Long-acting PEGylated Factor VIII for Hemophilia A Treatment," Blood 116(2):270-279, The American Society of Hematology, United States (Jul. 2010).
Milton et al., "Evaluation of Manometric Temperature Measurement as a Method of Monitoring Product Temperature During Lyophilization", PDS J Pharm Sci and Tech, 1997, 51: 7-16.
Muller, D. and Kontermann, R.E., "Recombinant Bispecific Antibodies for Cellular Cancer Immunotherapy," Current Opinion in Molecular Therapeutics 9(4):319-326, The Thomson Corporation, United States (Aug. 2007).
Nireesha G.R., et al., "Lyophilization/Freeze Drying—An Review," International Journal of Novel Trends in Pharmaceutical Sciences (IJNTPS), vol. 3 (4), Oct. 30, 2013, pp. 87-98.
Oganesyan, V., et al., "Structural Characterization of a Human Fc Fragment Engineered for Extended Serum Half-Life," Molecular Immunology 46(8-9):1750-1755, Pergamon Press, England (May 2009).
Parker et al., "Determination of the Influence of Primary Drying Rates on the Microscale Structural Attributes and Physicochemical Properties fo Protein Containing Lyophilized Products", Journal of Pharmaceutical Sciences, Nov. 2010, vol. 99, No. 11, pp. 4616-4629.
Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (Mar. 2007).
Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (Oct. 1995).
Schulte, S., "Half-life Extension through Albumin Fusion Technologies," Thrombosis Research 124(Suppl.2):S6-58, Pergamon Press, United States (Dec. 2009).
Scoffin, K., PharmTech.com, Equipment and Processing Report Issue 6, Apr. 15, 2015, 3 pages.
Shapiro, A.D., "Recombinant Factor IX-Fc Fusion Protein (rFIXFc) Demonstrates Safety and Prolonged Activity in a Phase 1/2a Study in Hemophilia B Patients," Blood 119(3):666-672, The American Society of Hematology, United States (Jan. 2012).
Shields, R.L., et al., "High Resolution Mapping of the Binding Site on Human IgG1 for Fc gamma RI, Fc gamma RII, Fc gamma RIII, and FcRn and Design of IgG1 Variants with Improved Binding to the Fc gamma R," The Journal of Biological Chemistry 276(9):6591-6604, American Society for Biochemistry and Molecular Biology, United States (Mar. 2001).
Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).
Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (Dec. 1994).
Tremain, Jeff, "How to Best Optimize Your Lyophilization Process Using Minimal Drug Substance", Retrieved From: «https://www.abbviecontractmfg.com/news-events/how-to-best-optimize-your-lyophilization-process-using-minimal-drug-substance.html», 5 Pages. (May 30, 2019).
Trussel, S., et al., "New Strategy for the Extension of the Serum Half-life of Antibody Fragments," Bioconjugate Chemistry 20(12):2286-2292, American Chemical Society, United States (Dec. 2009).
Vaccaro, C., et al., "Engineering the Fc region of Immunoglobulin G to Modulate in vivo Antibody Levels," Nature Biotechnology 23(10):1283-1288, Nature America Publishing, United States (Oct. 2005).
Wang, Y., et al., "Receptor-mediated Activation of a Proinsulin-transferrin Fusion Protein in Hepatoma Cells," Journal of Controlled Release 155(3):386-392, Elsevier B.V., Netherlands (Nov. 2011).
Ward, et al., "The Effector Functions of Immunoglobulins: Implications for Therapy", Therapeutic immunology, vol. 2, No. 2, pp. 77-94. (Apr. 1995).
Ward, "The Importance of Vacuum and the Control of Pressure in Freeze-Drying", 3rd Vacuum Symposium UK, Coventry, pp. 1-87 (Oct. 2012).
Weidler, B., et al., "Pharmakokinetische Merkmale als Kriterien fur den klinischen Einsatz von Hydroxyethylstarke," Arzneimittel-Forschung 41(5):494-498, Editio Cantor, Germany (May 1991).
U.S. Appl. No. 15/128,951 US20170173122A1 U.S. Pat. No. 10,772,942B2, filed Sep. 23, 2016 Jun. 22, 2017 Sep. 15, 2020, Brian M. Thome.
Cleland, "A Specific Molar Ratio of Stabilizer to Protein is Required for Storage Stability of a Lyophilized Monoclonal Antibody" Journal of Pharmaceutical Sciences, 2001, 90: 310-321.
Daugherty et al., "Formulation and Delivery Issues for Monoclonal Antibody Therapeutics", Current Trends in Monoclonal Antibody Development and Manufacturing, Biotechnology: Pharmaceutical Aspects, 2010, Chapter 8, pp. 103-129.
European Examination Report for European Patent Application No. 15769411.8, dated Jan. 15, 2024.
Wang et al., "Antibody Structure, Instability, and Formulation", Journal of Pharmaceutical Sciences, Jan. 1, 2007, 96(1): 1-26.
U.S. Appl. No. 15/128,951 2017/0173122 U.S. Pat. No. 10,772,942, filed Sep. 23, 2016 Jun. 22, 2017 Sep. 15, 2020, Brian M. Thome, Lyophilized Factor IX Formulations.
U.S. Appl. No. 16/995,173 2021/0069307, filed Aug. 17, 2020 Mar. 11, 2021, Brian M. Thome, Lyophilized Factor IX Formulations.

\* cited by examiner

SEQUENCE LISTING

<160> NUMBER OF SEQ ID NOS: 14

<210> SEQ ID NO 1
<211> LENGTH: 7583
<212> TYPE: DNA
<213> ORGANISM: Artificial Sequence
<220> FEATURE:
<223> OTHER INFORMATION: FIX-Fc Chain

<400> SEQUENCE: 1

| | | | |
|---|---|---|---|
| gcgcgcgttg acattgatta ttgactagtt attaatagta atcaattacg gggtcattag | 60 |
| ttcatagccc atatatggag ttccgcgtta cataacttac ggtaaatggc ccgcctggct | 120 |
| gaccgcccaa cgacccccgc ccattgacgt caataatgac gtatgttccc atagtaacgc | 180 |
| caatagggac tttccattga cgtcaatggg tggagtattt acggtaaact gcccacttgg | 240 |
| cagtacatca agtgtatcat atgccaagta cgccccctat tgacgtcaat gacggtaaat | 300 |
| ggcccgcctg gcattatgcc cagtacatga ccttatggga ctttcctact tggcagtaca | 360 |
| tctacgtatt agtcatcgct attaccatgg tgatgcggtt ttggcagtac atcaatgggc | 420 |
| gtggatagcg gtttgactca cggggatttc caagtctcca ccccattgac gtcaatggga | 480 |
| gtttgttttg gcaccaaaat caacgggact ttccaaaatg tcgtaacaac tccgccccat | 540 |
| tgacgcaaat gggcggtagg cgtgtacggt gggaggtcta tataagcaga gctctctggc | 600 |
| taactagaga acccactgct tactggctta tcgaaattaa tacgactcac tatagggaga | 660 |
| cccaagcttc gcgacgtacg gccgccacca tgcagcgcgt gaacatgatc atggcagaat | 720 |
| caccaggcct catcaccatc tgccttttag gatatctact cagtgctgaa tgtacaggtt | 780 |
| tgtttccttt tttaaaatac attgagtatg cttgcctttt agatatagaa atatctgatg | 840 |
| ctgtcttctt cactaaattt tgattacatg atttgacagc aatattgaag agtctaacag | 900 |
| ccagcacgca ggttggtaag tactgtggga acatcacaga ttttggctcc atgccctaaa | 960 |
| gagaaattgg ctttcagatt atttggatta aaacaaaga ctttcttaag agatgtaaaa | 1020 |
| ttttcatgat gttttctttt tgctaaaac taaagaatta ttcttttaca tttcagtttt | 1080 |
| tcttgatcat gaaaacgcca acaaaattct gaatcggcca agaggtata attcaggtaa | 1140 |
| attggaagag tttgttcaag ggaatctaga gagagaatgt atggaagaaa agtgtagttt | 1200 |
| tgaagaagca cgagaagttt ttgaaaacac tgaaagaaca actgaatttt ggaagcagta | 1260 |
| tgttgatgga gatcagtgtg agtccaatcc atgtttaaat ggcggcagtt gcaaggatga | 1320 |
| cattaattcc tatgaatgtt ggtgtccctt tggatttgaa ggaagaact gtgaattaga | 1380 |
| tgtaacatgt aacattaaga atggcagatg cgagcagttt tgtaaaaata gtgctgataa | 1440 |
| caaggtggtt tgctcctgta ctgagggata tcgacttgca gaaaaccaga agtcctgtga | 1500 |

```
accagcagtg ccatttccat gtggaagagt ttctgtttca caaacttcta agctcacccg    1560
tgctgagact gtttttcctg atgtggacta tgtaaattct actgaagctg aaaccatttt    1620
ggataacatc actcaaagca cccaatcatt taatgacttc actcgggttg ttggtggaga    1680
agatgccaaa ccaggtcaat tcccttggca ggttgttttg aatggtaaag ttgatgcatt    1740
ctgtggaggc tctatcgtta atgaaaaatg gattgtaact gctgcccact gtgttgaaac    1800
tggtgttaaa attacagttg tcgcaggtga acataatatt gaggagacag aacatacaga    1860
gcaaaagcga aatgtgattc gaattattcc tcaccacaac tacaatgcag ctattaataa    1920
gtacaaccat gacattgccc ttctggaact ggacgaaccc ttagtgctaa acagctacgt    1980
tacacctatt tgcattgctg acaaggaata cacgaacatc ttcctcaaat tggatctgg     2040 ctatgtaagt ggctggggaa gagtcttcca caaagggaga tcagctttag ttcttcagta    2100
ccttagagtt ccacttgttg accgagccac atgtcttcga tctacaaagt tcaccatcta    2160
taacaacatg ttctgtgctg gcttccatga aggaggtaga gattcatgtc aaggagatag    2220
tgggggaccc catgttactg aagtggaagg gaccagtttc ttaactggaa ttattagctg    2280
gggtgaagag tgtgcaatga aaggcaaata tggaatatat accaaggtgt cccggtatgt    2340
caactggatt aaggaaaaaa caaagctcac tgacaaaact cacacatgcc caccgtgccc    2400
agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520
ccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760
cctgccccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta aatgagaatt    3060
cagacatgat aagatacatt gatgagtttg gacaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat ccccgcgctg gaggatcatc    3240
cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga cagggtcac gtcgtcccgg accacaccgg cgaagtcgtc ctccacgaag    3600
tcccgggaga acccgagccg gtcggtccag aactcgaccg ctccggcgac gtcgcgcgcg    3660
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
```

```
ctcactactt ctggaatagc tcagaggcag aggcggcctc ggcctctgca taaataaaaa    3900
aaattagtca gccatggggc ggagaatggg cggaactggg cggagttagg ggcgggatgg    3960
gcggagttag gggcgggact atggttgctg actaattgag atgcatgctt tgcatacttc    4020
tgcctgctgg ggagcctggg gactttccac acctggttgc tgactaattg agatgcatgc    4080
tttgcatact tctgcctgct ggggagcctg gggactttcc acccctcgt cgagctagct    4140 tcgtgaggct ccggtgcccg tcagtgggca gagcgcacat cgcccacagt ccccgagaag    4200 ttgggggggag gggtcggcaa ttgaaccggt gcctagagaa ggtggcgcgg ggtaaactgg    4260
gaaagtgatg tcgtgtactg gctccgcctt tttcccgagg gtgggggaga accgtatata    4320
agtgcagtag tcgccgtgaa cgttcttttt cgcaacgggt ttgccgccag aacacaggta    4380
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
ggccttgcgc tttaggagcc ccttcgcctc gtgcttgagt tgaggcctgg cctgggcgct    4560
ggggccgccg cgtgcgaatc tggtggcacc ttcgcgcctg tctcgctgct ttcgataagt    4620
ctctagccat ttaaaatttt tgatgacctg ctgcgacgct ttttttctgg caagatagtc    4680
ttgtaaatgc gggccaggat ctgcacactg gtatttcggt ttttggggcc gcgggcggcg    4740
acggggcccg tgcgtcccag cgcacatgtt cggcgaggcg gggcctgcga gcgcggccac    4800
cgagaatcgg acggggtag tctcaagctg gccggcctgc tctggtgcct ggcctcgcgc    4860
cgccgtgtat cgccccgccc tgggcggcaa ggctggcccg tcggcacca gttgcgtgag    4920 cggaaagatg gccgcttccc ggccctgctc caggggctc aaaatggagg acgcggcgct    4980
cgggagagcg ggcgggtgag tcacccacac aaaggaaagg ggcctttccg tcctcagccg    5040
tcgcttcatg tgactccacg gagtaccggg cgccgtccag gcacctcgat tagttctgga    5100
gcttttggag tacgtcgtct ttaggttggg gggagggggtt ttatgcgatg gagtttcccc    5160
acactgagtg ggtggagact gaagttaggc cagcttggca cttgatgtaa ttctccttgg    5220
aatttgccct ttttgagttt ggatcttggt tcattctcaa gcctcagaca gtggttcaaa    5280 gttttttct tccatttcag gtgtcgtgaa cacgtggtcg cggccgcgcc gccaccatgg    5340
agacagacac actcctgcta tgggtactgc tgctctgggt tccaggttcc actggtgaca    5400
aaactcacac atgcccaccg tgcccagcac ctgaactcct gggaggaccg tcagtcttcc    5460
tcttcccccc aaaacccaag gacaccctca tgatctcccg gaccctgag gtcacatgcg    5520 tggtggtgga cgtgagccac gaagaccctg aggtcaagtt caactggtac gtggacggcg    5580
tggaggtgca taatgccaag acaaagccgc gggaggagca gtacaacagc acgtaccgtg    5640
tggtcagcgt cctcaccgtc ctgcaccagg actggctgaa tggcaaggag tacaagtgca    5700
aggtctccaa caaagccctc ccagccccca tcgagaaaac catctccaaa gccaagggc    5760 agccccgaga accacaggtg tacaccctgc cccatcccg cgatgagctg accaagaacc    5820
aggtcagcct gacctgcctg gtcaaaggct tctatcccag cgacatcgcc gtggagtggg    5880
agagcaatgg gcagccggag aacaactaca agaccacgcc tcccgtgttg gactccgacg    5940
gctccttctt cctctacagc aagctcaccg tggacaagag caggtggcag caggggaacg    6000
tcttctcatg ctccgtgatg catgaggctc tgcacaacca ctacacgcag aagagcctct    6060
ccctgtctcc gggtaaatga ctcgagagat ctggccggct gggcccgttt cgaaggtaag    6120
cctatcccta accctctcct cggtctcgat tctacgcgta ccggtcatca tcaccatcac    6180
cattgagttt aaacccgctg atcagcctcg actgtgcctt ctagttgcca gccatctgtt    6240
```

-continued

```
gtttgcccct cccccgtgcc ttccttgacc ctggaaggtg ccactcccac tgtcctttcc    6300
taataaaatg aggaaattgc atcgcattgt ctgagtaggt gtcattctat tctgggggat    6360
ggggtggggc aggacagcaa gggggaggat tgggaagaca atagcaggca tgctggggat    6420
gcggtgggct ctatggcttc tgaggcgaaa agaaccagtg gcggtaatac ggttatccac    6480
agaatcaggg gataacgcag gaaagaacat gtgagcaaaa ggccagcaaa aggccaggaa    6540
ccgtaaaaag gccgcgttgc tggcgttttt ccataggctc cgcccccctg acgagcatca    6600
caaaaatcga cgctcaagtc agaggtggcg aaacccgaca ggactataaa gataccaggc    6660
gtttccccct agaagctccc tcgtgcgctc tcctgttccg accctgccgc ttaccggata    6720
cctgtccgcc tttctccctt cgggaagcgt ggcgctttct catagctcac gctgtaggta    6780
tctcagttcg gtgtaggtcg ttcgctccaa gctgggctgt gtgcacgaac cccccgttca    6840
gcccgaccgc tgcgccttat ccggtaacta tcgtcttgag tccaacccgg taagacacga    6900
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggc tggcttaac tatgcggcat cagagcagat    7440
tgtactgaga gtgcaccata tgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                           7583
```

<210> SEQ ID NO 2
<211> LENGTH: 642
<212> TYPE: PRT
<213> ORGANISM: Artificial Sequence
<220> FEATURE:
<223> OTHER INFORMATION: FIX-Fc Chain

<400> SEQUENCE: 2

```
Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
            35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
```

-continued

```
            115                 120                 125
Pro Phe Pro Cys Gly Arg Val Ser Val Ser Gln Thr Ser Lys Leu Thr
        130                 135                 140
Arg Ala Glu Thr Val Phe Pro Asp Val Asp Tyr Val Asn Ser Thr Glu
145                 150                 155                 160
Ala Glu Thr Ile Leu Asp Asn Ile Thr Gln Ser Thr Gln Ser Phe Asn
                165                 170                 175
Asp Phe Thr Arg Val Val Gly Gly Glu Asp Ala Lys Pro Gly Gln Phe
            180                 185                 190
Pro Trp Gln Val Val Leu Asn Gly Lys Val Asp Ala Phe Cys Gly Gly
        195                 200                 205
Ser Ile Val Asn Glu Lys Trp Ile Val Thr Ala Ala His Cys Val Glu
210                 215                 220
Thr Gly Val Lys Ile Thr Val Val Ala Gly Glu His Asn Ile Glu Glu
225                 230                 235                 240
Thr Glu His Thr Glu Gln Lys Arg Asn Val Ile Arg Ile Ile Pro His
                245                 250                 255
His Asn Tyr Asn Ala Ala Ile Asn Lys Tyr Asn His Asp Ile Ala Leu
            260                 265                 270
Leu Glu Leu Asp Glu Pro Leu Val Leu Asn Ser Tyr Val Thr Pro Ile
        275                 280                 285
Cys Ile Ala Asp Lys Glu Tyr Thr Asn Ile Phe Leu Lys Phe Gly Ser
290                 295                 300
Gly Tyr Val Ser Gly Trp Gly Arg Val Phe His Lys Gly Arg Ser Ala
305                 310                 315                 320
Leu Val Leu Gln Tyr Leu Arg Val Pro Leu Val Asp Arg Ala Thr Cys
                325                 330                 335
Leu Arg Ser Thr Lys Phe Thr Ile Tyr Asn Asn Met Phe Cys Ala Gly
            340                 345                 350
Phe His Glu Gly Gly Arg Asp Ser Cys Gln Gly Asp Ser Gly Gly Pro
        355                 360                 365
His Val Thr Glu Val Glu Gly Thr Ser Phe Leu Thr Gly Ile Ile Ser
370                 375                 380
Trp Gly Glu Glu Cys Ala Met Lys Gly Lys Tyr Gly Ile Tyr Thr Lys
385                 390                 395                 400
Val Ser Arg Tyr Val Asn Trp Ile Lys Glu Lys Thr Lys Leu Thr Asp
                405                 410                 415
Lys Thr His Thr Cys Pro Pro Cys Pro Ala Pro Glu Leu Leu Gly Gly
            420                 425                 430
Pro Ser Val Phe Leu Phe Pro Pro Lys Pro Lys Asp Thr Leu Met Ile
        435                 440                 445
Ser Arg Thr Pro Glu Val Thr Cys Val Val Val Asp Val Ser His Glu
450                 455                 460
Asp Pro Glu Val Lys Phe Asn Trp Tyr Val Asp Gly Val Glu Val His
465                 470                 475                 480
Asn Ala Lys Thr Lys Pro Arg Glu Glu Gln Tyr Asn Ser Thr Tyr Arg
                485                 490                 495
Val Val Ser Val Leu Thr Val Leu His Gln Asp Trp Leu Asn Gly Lys
            500                 505                 510
Glu Tyr Lys Cys Lys Val Ser Asn Lys Ala Leu Pro Ala Pro Ile Glu
        515                 520                 525
Lys Thr Ile Ser Lys Ala Lys Gly Gln Pro Arg Glu Pro Gln Val Tyr
530                 535                 540
```

```
Thr Leu Pro Pro Ser Arg Asp Glu Leu Thr Lys Asn Gln Val Ser Leu
545                 550                 555                 560

Thr Cys Leu Val Lys Gly Phe Tyr Pro Ser Asp Ile Ala Val Glu Trp
                565                 570                 575

Glu Ser Asn Gly Gln Pro Glu Asn Asn Tyr Lys Thr Thr Pro Pro Val
            580                 585                 590

Leu Asp Ser Asp Gly Ser Phe Phe Leu Tyr Ser Lys Leu Thr Val Asp
        595                 600                 605

Lys Ser Arg Trp Gln Gln Gly Asn Val Phe Ser Cys Ser Val Met His
610                 615                 620

Glu Ala Leu His Asn His Tyr Thr Gln Lys Ser Leu Ser Leu Ser Pro
625                 630                 635                 640

Gly Lys

<210> SEQ ID NO 3
<211> LENGTH: 741
<212> TYPE: DNA
<213> ORGANISM: Artificial Sequence
<220> FEATURE:
<223> OTHER INFORMATION: Fc Portion

<400> SEQUENCE: 3
atggagacag acacactcct gctatgggta ctgctgctct gggttccagg ttccactggt      60
gacaaaactc acacatgccc accgtgccca gcacctgaac tcctgggagg accgtcagtc    120
ttcctcttcc ccccaaaacc caaggacacc ctcatgatct cccggacccc tgaggtcaca    180
tgcgtggtgg tggacgtgag ccacgaagac cctgaggtca agttcaactg gtacgtggac    240
ggcgtggagg tgcataatgc caagacaaag ccgcgggagg agcagtacaa cagcacgtac    300
cgtgtggtca gcgtcctcac cgtcctgcac caggactggc tgaatggcaa ggagtacaag    360
tgcaaggtct ccaacaaagc cctcccagcc cccatcgaga aaaccatctc caaagccaaa    420
gggcagcccc gagaaccaca ggtgtacacc ctgcccccat cccgcgatga gctgaccaag    480
aaccaggtca gcctgacctg cctggtcaaa ggcttctatc ccagcgacat cgccgtggag    540
tgggagagca atgggcagcc ggagaacaac tacaagacca cgcctcccgt gttggactcc    600
gacggctcct tcttcctcta cagcaagctc accgtggaca agagcaggtg gcagcagggg    660
aacgtcttct catgctccgt gatgcatgag gctctgcaca accactacac gcagaagagc    720
ctctccctgt ctccgggtaa a                                              741

<210> SEQ ID NO 4
<211> LENGTH: 227
<212> TYPE: PRT
<213> ORGANISM: Artificial Sequence
<220> FEATURE:
<223> OTHER INFORMATION: Fc Portion

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 11
<212> TYPE: PRT
<213> ORGANISM: Artificial Sequence
<220> FEATURE:
<223> OTHER INFORMATION: Core sequence of albumin-binding peptides

<400> SEQUENCE: 5

Asp Ile Cys Leu Pro Arg Trp Gly Cys Leu Trp
1               5                   10

<210> SEQ ID NO 6
<211> LENGTH: 32
<212> TYPE: PRT
<213> ORGANISM: Artificial Sequence
<220> FEATURE:
<223> OTHER INFORMATION: CTP peptide

<400> SEQUENCE: 6

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 7
<211> LENGTH: 28
<212> TYPE: PRT
<213> ORGANISM: Artificial Sequence
<220> FEATURE:
<223> OTHER INFORMATION: CTP peptide

<400> SEQUENCE: 7

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

```
<210> SEQ ID NO 8
<211> LENGTH: 20
<212> TYPE: PRT
<213> ORGANISM: Artificial Sequence
<220> FEATURE:
<223> OTHER INFORMATION: PAS peptide

<400> SEQUENCE: 8

Ala Ser Pro Ala Ala Pro Ala Pro Ala Ser Pro Ala Ala Pro Ala Pro
1               5                   10                  15

Ser Ala Pro Ala
            20

<210> SEQ ID NO 9
<211> LENGTH: 20
<212> TYPE: PRT
<213> ORGANISM: Artificial Sequence
<220> FEATURE:
<223> OTHER INFORMATION: PAS peptide

<400> SEQUENCE: 9

Ala Ala Pro Ala Ser Pro Ala Pro Ala Ala Pro Ser Ala Pro Ala Pro
1               5                   10                  15

Ala Ala Pro Ser
            20

<210> SEQ ID NO 10
<211> LENGTH: 20
<212> TYPE: PRT
<213> ORGANISM: Artificial Sequence
<220> FEATURE:
<223> OTHER INFORMATION: PAS peptide

<400> SEQUENCE: 10

Ala Pro Ser Ser Pro Ser Pro Ser Ala Pro Ser Ser Pro Ser Pro Ala
1               5                   10                  15

Ser Pro Ser Ser
            20

<210> SEQ ID NO 11
<211> LENGTH: 19
<212> TYPE: PRT
<213> ORGANISM: Artificial Sequence
<220> FEATURE:
<223> OTHER INFORMATION: PAS peptide

<400> SEQUENCE: 11

Ala Pro Ser Ser Pro Ser Pro Ser Ala Pro Ser Ser Pro Ser Pro Ala
1               5                   10                  15

Ser Pro Ser

<210> SEQ ID NO 12
<211> LENGTH: 20
<212> TYPE: PRT
<213> ORGANISM: Artificial Sequence
<220> FEATURE:
<223> OTHER INFORMATION: PAS peptide

<400> SEQUENCE: 12

Ser Ser Pro Ser Ala Pro Ser Pro Ser Ser Pro Ala Ser Pro Ser Pro
1               5                   10                  15

Ser Ser Pro Ala
            20
```

```
<210> SEQ ID NO 13
<211> LENGTH: 24
<212> TYPE: PRT
<213> ORGANISM: Artificial Sequence
<220> FEATURE:
<223> OTHER INFORMATION: PAS peptide

<400> SEQUENCE: 13

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 14
<211> LENGTH: 20
<212> TYPE: PRT
<213> ORGANISM: Artificial Sequence
<220> FEATURE:
<223> OTHER INFORMATION: PAS peptide

<400> SEQUENCE: 14

Ala Ser Ala Ala Ala Pro Ala Ala Ala Ser Ala Ala Ala Ser Ala Pro
1               5                   10                  15

Ser Ala Ala Ala
            20
```

LYOPHILIZED FACTOR IX FORMULATIONS

RELATED APPLICATIONS

This application is a continuation of U.S. patent application Ser. No. 15/128,951, filed Sep. 23, 2016, now U.S. Pat. No. 10,772,942, which is a 35 U.S.C. § 371 filing of International Patent Application No. PCT/US2015/022141, filed Mar. 24, 2015, which claims the benefit of U.S. Provisional Patent Application No. 61/969,801, filed Mar. 24, 2014, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Aug. 17, 2020, is named 709074_SA9-449USCON_ST25.txt and is 22,024 bytes in size.

BACKGROUND

The present invention relates generally to the field of therapeutics for hemostatic disorders.

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual will suffer from spontaneous bleeding in the joints, which produces severe pain and debilitating immobility; bleeding into muscles results in the accumulation of blood in those tissues; spontaneous bleeding in the throat and neck can cause asphyxiation if not immediately treated; renal bleeding; and severe bleeding following surgery, minor accidental injuries, or dental extractions also are prevalent.

Normal in vivo blood coagulation at minimum requires the serine proteases Factors II (prothrombin), VII, IX, X and XI (soluble plasma proteins); cofactors including the transmembrane protein tissue factor and the plasma proteins Factors V and VIII; fibrinogen, the transglutaminase Factor XIII, phospholipid (including activated platelets), and calcium. Additional proteins including kallikrein, high molecular weight kininogen, and Factor XII are required for some in vitro clotting tests, and can play a role in vivo under pathologic conditions.

In hemophilia, blood clotting is disturbed by a lack of certain plasma blood clotting factors. Hemophilia B is caused by a deficiency in Factor IX that can result from either the decreased synthesis of the Factor IX protein or a defective molecule with reduced activity. The treatment of hemophilia occurs by replacement of the missing clotting factor by exogenous factor concentrates highly enriched in Factor IX. However, generating such a concentrate from blood is fraught with technical difficulties, as is described below.

Purification of Factor IX from plasma (plasma derived Factor IX; pdFIX) almost exclusively yields active Factor IX. However, such purification of Factor IX from plasma is very difficult because Factor IX is only present in low concentration in plasma (5 μg/mL. Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant factor IX (rFIX) is also available, but suffers from the same short half-life and need for frequent dosing (e.g., 2-3 times per week for prophylaxis) as pdFIX. rFIX also has a lower incremental recovery (K value) compared to pdFIX, which necessitates the use of higher doses of rFIX than those for pdFIX.

Reduced mortality, prevention of joint damage and improved quality of life have been important achievements due to the development of plasma-derived and recombinant Factor IX. Prolonged protection from bleeding would represent another key advancement in the treatment of hemophilia B subjects. However, to date, no products that allow for prolonged protection have been developed. Therefore, there remains a need for improved methods of treating hemophilia due to Factor IX deficiency that are more tolerable and more effective than current therapies.

In particular, there remains a need for improved lyophilized FIX formulations with higher drug product strength, longer shelf life, reduced lyophilization process time, and shorter reconstitution time.

BRIEF SUMMARY OF THE INVENTION

The present invention is directed to a pre-lyophilization formulation comprising: (a) a Factor IX (FIX) polypeptide having FIX coagulation activity; (b) a buffering agent; (c) a stabilizing agent; (d) a bulking agent; and (e) a surfactant, wherein the formulation has a fill volume of less than about 5 mL, less than about 4 mL, or less than about 3 mL and wherein each of (a)-(e) are at an amount per vial (mg/vial) sufficient to allow (1) improved stability of the FIX polypeptide when lyophilized; (2) reduced reconstitution time when lyophilized; (3) reduced splashing onto a stopper comprising the formulation; (4) reduced lyophilization cycle time; (5) increased shelf-life of a lyophilate prepared from the pre-lyophilization formulation at room temperature; or (6) any combinations thereof, compared to a reference pre-lyophilization formulation, wherein the reference formulation comprises (a)-(e) at the amount per vial identical to the pre-lyophilization formulation, but has at least a 5 mL fill volume. In a particular embodiment, the fill volume of the formulation is about 2.65 mL.

In some embodiments, the pre-lyophilization formulation comprises at least 100 IU/vial of the FIX polypeptide. In some embodiments, the pre-lyophilization formulation comprises about 200 IU/vial to about 10,000 IU/vial of the FIX polypeptide.

In some embodiments, the FIX polypeptide comprises wild-type FIX. In some embodiments, the FIX polypeptide further comprises a heterologous moiety fused to wild-type FIX. In one embodiment, the heterologous moiety is a moiety extending half-life of FIX. In another embodiment, the heterologous moiety comprises a polypeptide or a non-polypeptide moiety. In one embodiment, the moiety extending half-life of FIX comprises an FcRn binding partner or an Fc region. In one embodiment, the FIX polypeptide is at least about 80%, at least about 85%, at least about 90%, at least about 95%, or 100% identical to SEQ ID NO: 2.

In some embodiments, the fill volume is about 4 mL, about 3.5 mL, about 3.0 mL, about 2.9 mL, about 2.8 mL, about 2.7 mL, about 2.65 mL, about 2.6 mL, about 2.5 mL, about 2.4 mL, about 2.3 mL, about 2.2 mL, about 2.1 mL, or about 2.0 mL.

In some embodiments, the reduced reconstitution time is less than 1.5 minute, less than 1 minute, less than 50 seconds, less than 40 seconds, less than 30 seconds, less than 20 seconds, or less than 10 seconds.

In some embodiments, the buffering agent is L-histidine. In one embodiment, the buffering agent is at a concentration (mg/mL) between about 3 mg/mL and about 15 mg/mL. In another embodiment, the buffering agent is at a concentration between about 8 mg and about 39 mg per vial.

In some embodiments, the stabilizing agent is sucrose. In one embodiment, the stabilizing agent is at a concentration (mg/mL) between 10 mg/mL and about 50 mg/mL. In another embodiment, the stabilizing agent is at a concentration between about 27 mg and about 132 mg per vial.

In some embodiments, the bulking agent is mannitol. In one embodiment, the bulking agent is at a concentration (mg/mL) between 20 mg/mL and about 100 mg/mL. In another embodiment, the bulking agent is at a concentration between about 53 mg per vial and about 265 mg per vial.

In some embodiments, the surfactant is polysorbate 20. In one embodiment, the surfactant is at a concentration (mg/mL) between 0.01 mg/mL and about 5 mg/mL. In another embodiment, the surfactant is at a concentration between about 0.03 mg and about 13 mg per vial.

In one aspect, the invention is directed to pre-lyophilization formulation comprising: (a) about 80 to about 2,750 IU/mL of rFIXFc; (b) about 7.76 mg/mL of L-histidine; (c) about 47.6 mg/mL of mannitol; (d) about 23.8 mg/mL of sucrose; and, (e) about 0.2 mg/mL of polysorbate-20.

The present invention is further directed to a lyophilate powder comprising a FIX polypeptide, a buffering agent, a stabilizing agent, a bulking agent, a surfactant, or any combinations thereof.

In some embodiment, the residual moisture level of the lyophilate powder is below 1%.

In one embodiment, the lyophilate powder comprises: (a) a FIX polypeptide at an amount between about 2 mg per vial and about 150 mg per vial; (b) a buffering agent at an amount between 10 mg per vial and about 30 mg per vial; (c) a bulking agent at an amount between 70 mg vial and about 200 mg per vial; (d) a stabilizing agent at an amount between 30 mg per vial and 100 mg per vial; and (e) a surfactant at an amount between 0.05 mg per vial and about 5 mg per vial.

In another embodiment, the lyophilate powder comprises: (a) the lyophilized FIX polypeptide at an amount between about 2.2 mg per vial and about 125 mg per vial; (b) the buffering agent at an amount between about 12.5 mg per vial and 25 mg per vial; (c) the stabilizing agent at an amount between about 32.5 mg per vial and 80 mg per vial; (d) the bulking agent at an amount between about 75 mg per vial and 150 mg per vial; and (e) the surfactant at an amount between about 0.1 mg/mL and about 2 mg/mL.

In another embodiment, the lyophilate powder comprises: (a) about 2.2 to about 125 mg/vial of the FIX polypeptide; (b) about 20.6 mg/vial of L-histidine; (c) about 126.1 mg/vial of mannitol; (d) about 63.1 mg/vial of sucrose; and, (e) about 0.53 mg/vial of polysorbate-20;

The present invention is also directed to a reconstituted formulation comprising the lyophilate powder described herein reconstituted by a reconstitution buffer.

In one embodiment, the reconstituted formulation comprises: (a) the FIX polypeptide at a concentration between about 0.9 mg/mL and about 50 mg/mL; (b) the buffering agent at a concentration between 1.5 mg/mL and about 7.5 mg/mL; (c) the bulking agent at a concentration between 10 mg/mL and about 50 mg/mL; (d) the stabilizing agent at a concentration between 5 mg/mL and 25 mg/mL per vial; and (e) the surfactant at a concentration between 0.005 mg/mL and about 2.5 mg/mL.

In another embodiment, the reconstituted formulation comprises: (a) the FIX polypeptide at a concentration between about 0.9 mg/mL and about 50 mg/mL; (b) the buffering agent at a concentration of about 3.88 mg/mL; (c) the bulking agent at a concentration of about 23.8 mg/mL; (d) the stabilizing agent at a concentration of about 11.9 mg/mL; (e) the surfactant at a concentration of about 0.1 mg/mL; and (0 the reconstitution buffer.

In another embodiment, the reconstituted formulation comprises: (a) the FIX polypeptide at a concentration between about 80 IU/mL and about 2,750 IU/mL; (b) the buffering agent at a concentration of about 25 mM; (c) the bulking agent at a concentration of about 131 mM; (d) the stabilizing agent at a concentration of about 35 mM; (e) the surfactant at a concentration of 0.01% (w/v); and (0 the reconstitution buffer.

The present invention further pertains to a method of administering a FIX polypeptide to a hemophilia B patient in need thereof, or a method of preventing, treating, ameliorating, or managing hemophilia B in a patient in need thereof, comprising administering to the patient the reconstituted formulations described herein.

The present invention is also directed to a method of producing a lyophilate powder comprising a FIX polypeptide comprising lyophilizing the pre-lyophilization formulations described herein.

In one aspect, the present invention is directed to a method of lyophilizing a FIX polypeptide comprising: (a) a "freezing step" comprising freezing a pre-lyophilization formulation comprising the FIX polypeptide and an aqueous solvent; (b) a "vacuum step" comprising reducing the pressure of the frozen pre-lyophilization formulation by an amount effective to remove the aqueous solvent from the frozen pre-lyophilization formulation; and, (c) a single "drying step" comprising increasing the temperature of the frozen pre-lyophilization formulation above the collapse temperature, thereby producing a lyophilate powder. In some embodiments, the pre-lyophilization formulation is aseptically filtered and aseptically filled into a vial prior to step (a).

In another aspect, the present invention is directed to methods of producing a lyophilate powder comprising a FIX polypeptide, comprising: (a) a "freezing step" comprising freezing a pre-lyophilization formulation comprising a FIX polypeptide by ramping down the temperature for about 2 hours to a freezing temperature of about −55° C., and holding the freezing temperature for about 2 hours; (a') an "annealing step" comprising ramping up for about 1.5 hours the temperature of the frozen pre-lyophilization formulation of step (a) to an annealing temperature of about −6° C., holding the annealing temperature for about 3 hours, and ramping down the temperature for about 1.5 hours to about −55° C.; (b) a "vacuum step" comprising holding the frozen pre-lyophilization formulation of step (a') at about −55° C. for two hours at atmospheric pressure and ramping down the pressure for about 2 hours to about 0.33 mbar; and, (c) a single "drying step" comprising ramping up for 3 hours the temperature of the frozen pre-lyophilization formulation of step (b) to about 40° C., while holding the pressure at about 0.33 mbar, and holding the temperature of the frozen pre-lyophilization formulation at about 40° C. for about 25 hours, while holding the pressure at about 0.33 mbar, thereby producing the lyophilate powder.

In a further aspect, the lyophilate powder has one or more characteristics selected from the group consisting of: (1) improved stability of the FIX polypeptide when lyophilized; (2) reduced reconstitution time when lyophilized; (3)

reduced splashing onto a stopper comprising the formulation; (4) reduced lyophilization cycle time; (5)
increased shelf-life of a lyophilate prepared from the pre-lyophilization formulation at room temperature; or (6) any combinations thereof, In one aspect, the disclosure provides a method of stabilizing a lyophilate powder comprising a FIX polypeptide, comprising lyophilizing a pre-lyophilization formulation according to the methods described herein, wherein the lyophilate powder is stabilized as measured by Size Exclusion Chromatography (SEC) with respect to a lyophilate powder prepared by using a lyophilization method comprising more than one drying step.

In another aspect, the disclosure provides a method of increasing the shelf-life of a lyophilate powder comprising a FIX polypeptide, comprising lyophilizing a pre-lyophilization formulation according to the methods described herein, wherein the shelf-life of the lyophilate powder is increased as measured by SEC and/or FIX clotting activity assay with respect to the shelf-life of a lyophilate powder prepared by using a lyophilization method comprising more than one drying step.

This disclosure also provides a method to decrease the reconstitution time of a lyophilate powder comprising a FIX polypeptide, comprising lyophilizing a pre-lyophilization formulation according to the methods described herein, wherein the reconstitution time of the lyophilate powder is decreased with respect to the reconstitution time of a lyophilate powder prepared by using a lyophilization method comprising more than one drying step.

This disclosure further provides a method to reduce lyophilization process time of producing a lyophilate powder comprising a FIX polypeptide, comprising lyophilizing a pre-lyophilization formulation according to the methods described herein, wherein the lyophilization process time of the pre-lyophilization formulation is reduced with respect to the lyophilization process time of producing a lyophilate powder using a lyophilization method comprising more than one drying step.

DETAILED DESCRIPTION

Figure 1:
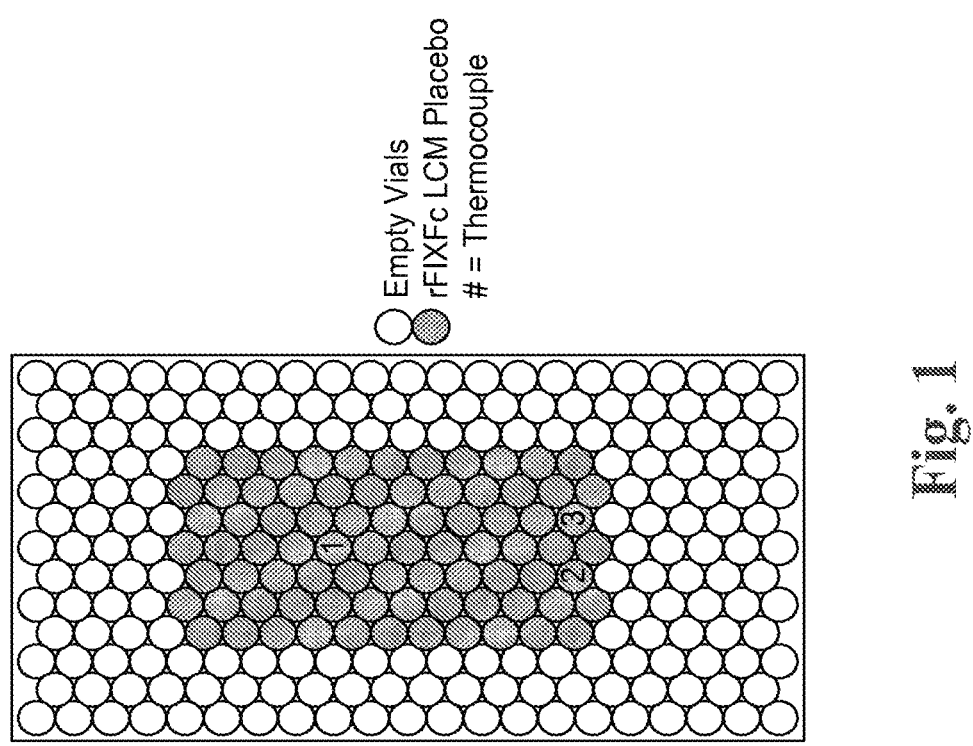
FIG. 1 shows the vial loading pattern for each lyophilization cycle. The numbers 1, 2, and 3 indicate the thermocouple locations.

This disclosure provides, among other things, pre-lyophilization formulations, reconstituted formulations, and lyophilate powder compositions comprising a Factor IX (FIX) polypeptide. The disclosure also provides lyophilization methods for producing lyophilate powder comprising a FIX polypeptide. Also provided are methods of stabilizing a lyophilate powder comprising a FIX polypeptide, method to increase the shelf-life of a lyophilate powder comprising a FIX polypeptide, method to decrease the reconstitute time of a lyophilate powder comprising a FIX polypeptide, and method to reduce lyophilization process time of a pre-lyophilization formulation comprising a FIX polypeptide. In addition, the disclosure provides methods of preventing, treating, ameliorating, or managing hemophilia B in a patient in need of by administering a reconstituted formulation comprising a FIX polypeptide.

Definitions

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of, and the value will depend on how limitations of the measuring system. When the term "about" is used in conjunction with a numerical range, it modifies that range by extending the boundaries above and below the numerical values set forth. In general, the term "about" can modify a numerical value above and below the stated value by a variance of, e.g., 10 percent or 20 percent, up or down (higher or lower). Unless otherwise stated, the meaning of "about" should be assumed to be within an acceptable error range for the particular value for the formulation or composition.

The term "polypeptide," "peptide" and "protein" are used interchangeably and refer to a polymeric compound comprised of covalently linked amino acid residues.

The term "polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses.

The term "administering," as used herein, means to, e.g., prescribe or give a pharmaceutical composition comprising an FIX polypeptide to a subject. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration. A pharmaceutical composition comprising an FIX polypeptide can comprise one or more excipients, as described herein. Advantages of the methods, compositions, and pharmaceutical kits provided herein include: improved regimen compliance; reduced break through bleeds; increased protection of joints from bleeds; prevention of joint damage; reduced morbidity; reduced mortality; prolonged protection from bleeding; decreased thrombotic events; and improved quality of life. Administering includes parenteral administration. In some embodiments, the parenteral administration is intravenous or subcutaneous administration.

The term "treatment" or "treating" as used herein means amelioration or reduction of one or more symptoms of bleeding diseases or disorders including, but not limited to, hemophilia B. In one embodiment, "treatment of" or "treating" a bleeding disease or disorder includes prevention of one or more symptoms of a bleeding disease or disorder. In a bleeding disease or disorder caused by a FIX deficiency (e.g., a low baseline FIX activity), the term "treatment" or "treating" can mean FIX replacement therapy. By administering a FIXFc polypeptide to a subject, the subject can achieve and/or maintain a plasma trough level of a FIX activity at about 1 IU/dl or above 1 IU/dl. In other embodiments, "treatment" or "treating" means reduction of the frequency of one or more symptoms of bleeding diseases or disorders, e.g., spontaneous or uncontrollable bleeding episodes. "Treatment," however, need not be a cure.

"Patient" as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia B, who are susceptible to uncontrolled bleeding episodes, e.g., hemophilia, or any combinations thereof. Patients can also include an individual who is in danger of one or more uncontrollable bleeding episodes prior to a certain activity, e.g., a surgery, a sport activity, or any strenuous activities. The patient can have a baseline FIX activity less than 1%, less than 0.5%, less than 2%, less than 2.5%, less than 3%, or less than 4%. Patients also include pediatric humans. Pediatric patients are birth to 20 years, preferably birth to 18 years, birth to 16 years, birth to 15 years, birth to 12 years, birth to 11 years, birth to 6 years, birth to 5 years, birth to 2 years, and 2 to 11 years of age.

"Baseline," as used herein, is the lowest measured plasma Factor IX level in a subject prior to administering a dose. The Factor IX plasma levels can be measured at two time points prior to dosing: at a screening visit and immediately prior to dosing. Alternatively, (a) the baseline in subjects whose pretreatment FIX activity is <1%, who have no detectable FIX antigen, and have nonsense genotypes can be defined as 0%, (b) the baseline for subjects with pretreatment FIX activity <1% and who have detectable FIX antigen can be set at 0.5%, (c) the baseline for subjects whose pretreatment FIX activity is between 1-2% is Cmin (the lowest activity throughout the PK study), and (d) the baseline for subjects whose pretreatment FIX activity is >2% can be set at 2%. Activity above the baseline pre-dosing can be considered residue drug from prior treatment, and can be decayed to baseline and subtracted from the PK data following rFIXFBP dosing.

"Trough," as used herein, is the lowest plasma Factor IX activity level reached after administering a dose of chimeric polypeptide of the invention or another Factor IX molecule and before the next dose is administered, if any. Trough is used interchangeably herein with "threshold." Baseline Factor IX levels are subtracted from measured Factor IX levels to calculate the trough level.

As used herein, the term "half-life" refers to a biological half-life of a particular polypeptide in vivo. Half-life can be represented by the time required for half the quantity administered to a subject to be cleared from the circulation and/or other tissues in the animal.

The terms "long-acting" and "long-lasting" are used interchangeably herein. In one embodiment, the term "long-acting" or "long-lasting" indicates that a FIX activity as a result of administration of the rFIXFBP polypeptide is longer than the FIX activity of a wild-type FIX (e.g., BENEFIX® or plasma-derived FIX ("pdFIX")). The "longer" FIX activity can be measured by any known methods in the art, e.g., aPTT assay, chromogenic assay, ROTEM, TGA, and etc. In one embodiment, the "longer" FIX activity can be shown by the $T_{1/2beta}$ (activity). In another embodiment, the "longer" FIX activity can be inferred by the level of FIX antigen present in plasma, e.g., by the $T_{1/2beta}$ (antigen).

The terms "lyophilate," "lyophilate powder," "lyophilized product," or "product cake," as used herein, denote a formulation which is manufactured by freeze-drying methods. The solvent (e.g. water) is removed by freezing following sublimation under vacuum and desorption of residual water at elevated temperature. In the pharmaceutical field, the lyophilate is present as a powder or a physical stable cake. The lyophilate is characterized by a fast dissolution after addition of a reconstitution medium.

The term "pre-lyophilization formulation" or "lyophilization feedstock" as used herein denotes a liquid formulation before the solvent (e.g., water) is removed by a freeze-drying method. The "fill volume" of a pre-lyophilization formulation is the total volume of the liquid formulation prior to lyophilization.

"$T_{1/2\beta}$," or "$T_{1/2\ beta}$" or "Beta HL," as used herein, is half-life associated with elimination phase, $t_{1/2\beta}=(\ln 2)/$ elimination rate constant associated with the terminal phase. The $T_{1/2\ beta}$ can be measured by FIX activity or by FIX antigen level in plasma. The $T_{1/2}$ beta based on activity is shown as $T_{1/2\ beta}$ (activity), and the $T_{1/2\ beta}$ based on the FIX antigen level can be shown as $T_{1/2\ beta}$ (antigen). Both $T_{1/2\ beta}$ (activity) and $T_{1/2\ beta}$ (antigen) can be shown as ranges or a geometric mean.

The term "reconstituted formulation" or "post-reconstitution composition" as used herein denotes a formulation which is lyophilized and re-dissolved by addition of a diluent. The diluent can contain, without limitation, water for injection (WFI), bacteriostatic water for injection (BWFI), sodium chloride solutions (e.g., 0.9% (w/v) NaCl), glucose solutions (e.g., 5% glucose), surfactant containing solutions (e.g., 0.01% polysorbate 20 or polysorbate 80), a pH-buffered solution (e.g. phosphate-buffered solutions) and combinations thereof.

The Lyophilization Process in General

Lyophilization, or freeze-drying, is a process widely used in the pharmaceutical industry for the preservation of biological and pharmaceutical materials. The lyophilization process, also known as the lyophilization cycle, is traditionally divided into three distinct stages: freezing, primary drying, and secondary drying. "Lyophilizing," as used herein, refers to the entire process of lyophilization, including both the freezing steps and the drying steps.

In lyophilization, water present in a material is converted to ice during a freezing step and then removed from the material by direct sublimation under low-pressure conditions during a primary drying step. During freezing, however, not all of the water is transformed to ice. Some portion of the water is trapped in a matrix of solids containing, for example, formulation components and/or the active ingredient. The excess bound water within the matrix can be reduced to a desired level of residual moisture during a secondary drying step. All lyophilization steps, freezing, primary drying and secondary drying, are determinative of the final product properties. The primary drying is typically the longest step in a lyophilization process, therefore, optimization of this portion of the process has significant economic effect.

In certain aspects of the invention, the lyophilization process only comprises the primary drying step.

In certain aspects of the invention, the lyophilization process also comprises a separate "vacuum step" between the freezing step and the primary drying step.

In other aspects of the invention, the lyophilization process further comprises an "annealing step" between the freezing step and the primary drying step.

The term "annealing step" as used herein refers to a step in the lyophilization process of a polypeptide preparation undergoing lyophilization, prior to the drying step of the preparation, in which the temperature of the preparation is raised from a lower temperature to a higher temperature and then cooled again after a period of time.

Cycle and formulation optimization has traditionally been performed to assure that the product temperature during primary drying would never exceed the collapse temperature. The term "collapse temperature" as used herein refers to the product temperature during freeze-drying above which product cake begins to lose its original structure. Above the collapse temperature, product could experience slow sporadic bubbling, swelling, foaming, cavitation, fenestration, gross collapse, retraction and beading that may have consequences on the appearance of the product. As a result, Collapse may result in poor product stability, long drying times, uneven drying and loss of texture. See, e.g., US 2010/0041870.

Lyophilized product in accordance with the present invention can be assessed based on product quality analysis, reconstitution time, quality of reconstitution, high molecular weight, moisture, glass transition temperature ($T_g$), and biological or biochemical activity. Typically, product quality analysis includes product degradation rate analysis using methods including, but not limited to, size exclusion chromatography (SEC), cation exchange-HPLC (CEX-HPLC), X-ray diffraction (XRD), modulated differential scanning calorimetry (mDSC), reversed phase HPLC (RP-HPLC), multi-angle light scattering detector (MALS), fluorescence, ultraviolet absorption, nephelometry, capillary electrophoresis (CE), SDS-PAGE, and combinations thereof. In some embodiments, evaluation of lyophilized product in accordance with the present invention includes a step of evaluating cake appearance. Additionally, lyophilized product may be assessed based on biological or biochemical activities of the product, typically, after reconstitution.

Lyophilized Factor IX Formulations

This disclosure provides pre-lyophilization, lyophilized, and post-reconstitution formulations, or pharmaceutical compositions, comprising a FIX polypeptide.

In certain aspects of the invention, the formulations disclosed herein comprise a FIX polypeptide, a buffering agent, a stabilizing agent, a bulking agent, and a surfactant, or any combinations thereof. The formulation can also contain any other agents that are useful for pharmaceutical formulation.

Factor IX (FIX) Polypeptide

The FIX polypeptide or FIX protein useful for the formulation is a functional Factor FIX protein in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature FIX (minus the signal sequence and propeptide), and mature FIX with an additional Met at the N-terminus. FIX can be made by recombinant means ("recombinant Factor IX" or "rFIX"), i.e., it is not naturally occurring or derived from plasma.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased dotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which can be used for polymer (e.g., PEG) conjugation, at page 11, paragraph [0043] to page 13, paragraph The FIX polypeptides described in International Application No. PCT/US2011/043569 filed Jul. 11, 2011 and published as WO 2012/006624 on Jan. 12, 2012 are also incorporated herein by reference in its entirety.

In certain embodiments, the FIX polypeptide comprises wild-type FIX. In some embodiments, the FIX polypeptide further comprises a heterologous moiety fused to wild-type FIX. In certain embodiments, the heterologous moiety is a moiety extending half-life of FIX. In certain embodiments, the heterologous moiety comprises a polypeptide or a non-polypeptide moiety.

In other embodiments, the FIX polypeptide is a long-acting FIX polypeptide. A long-acting FIX polypeptide can comprise a FIX portion and a non FIX portion, e.g., a heterologous moiety that is capable of extending in vivo or in vitro half-life of the FIX polypeptide. Exemplary non-FIX portions include, e.g., Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. Exemplary long-acting FIX polypeptides of the invention include, e.g., Factor IX-Fc polypeptides, Factor IX-albumin polypeptides, Factor IX-PAS polypeptides, Factor IX-transferrin polypeptides, Factor IX-CTP polypeptides, Factor IX-PEG polypeptides, Factor IX-HES polypeptides, Factor IX-albumin binding polypeptide polypeptides, or Factor IX-albumin-binding small molecule polypeptides.

In one embodiment, the FIX polypeptide is rFIXFc, a recombinant fusion protein comprised of human coagulation Factor IX (FIX) and an Fc domain of a human antibody (IgG1 isotype). See, e.g., PCT Application No. PCT/US2011/043569, filed Jul. 11, 2011 and published as WO 2012/006624, which is incorporated herein by reference in its entirety. The rFIXFc polypeptide is a heterodimeric protein with a FIXFc single chain (FIXFc-sc) and an Fc single chain (Fc-sc) bound together through two disulfide bonds in the hinge region of Fc. rFIXFc requires two protein subunits, FIXFc-sc (642 amino acids, SEQ ID NO:2) and Fc-sc (227 amino acids, SEQ ID NO:4), to assemble within a transfected cell line to form the final protein product, rFIXFc. The polynucleotide sequences encoding FIXFc-sc and Fc-sc are presented as SEQ ID NO:1 and SEQ ID NO:3, respectively.

In certain embodiments, the Factor IX portion of rFIXFc has a primary amino acid sequence that is identical to the Thr148 allelic form of plasma derived Factor IX and has structural and functional characteristics similar to endogenous Factor IX. The Fc domain of rFIXFc contains the hinge, CH2 and CH3 regions of IgG1. The assembled heterodimer mature form of rFIXFc contains 869 amino acids with a molecular weight of approximately 98 kilodaltons. In some embodiments, the rFIXFc polypeptide comprises an amino acid sequence at least 90%, 95%, or 100% identical to amino acids 1 to 642 of SEQ ID NO:2.

In one embodiment, the second portion fused to FIX is an FcRn binding partner. In another embodiment, an FcRn binding partner fused to FIX is an Fc fragment. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., Nature 372:379 (1994), incorporated herein by reference in its entirety). The major contact area of the Fc with the FcRn is near the junction of the CH2 and CH3 domains. Fc-FcRn contacts are all within a single Ig heavy chain. The FcRn binding partners include, e.g., whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., J. Exp. Med. 180: 2377 (1994), incorporated herein by reference in its entirety.) An Fc can comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

Fc (or Fc portion of a chimeric polypeptide) can contain one or more mutations, and combinations of mutations.

Fc (or Fc portion of a chimeric polypeptide) can contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of US 2009/0264627 A1, which is incorporated herein by reference in its entirety; and the mutants disclosed at page 2, paragraphs [0014] to [0021] of US 20090163699 A1, which is incorporated herein by reference in its entirety.

Fc (or Fc portion of a chimeric polypeptide) can also include, e.g., the following mutations: The Fc region of IgG can be modified according to well recognized procedures such as site directed mutagenesis and the like to yield modified IgG or Fc fragments or portions thereof that will be bound by FcRn. Such modifications include, e.g., modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids can be substituted for the wildtype amino acids at the positions specified above. Mutations can be introduced singly into Fc giving rise to more than one hundred FcRn binding partners distinct from native Fc. Additionally, combinations of two, three, or more of these individual mutations can be introduced together, giving rise to hundreds more FcRn binding partners. Certain of these mutations can confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie, Therapeutic Immunology 2:77 (1995), which is incorporated herein by reference in its entirety; and Armour et al., Eur. J. Immunol. 29:2613 (1999), which is incorporated herein by reference in its entirety). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Mutations believed to impart an increased affinity for FcRn include, e.g., T256A, T307A, E380A, and N434A (Shields et al., J. Biol. Chem. 276:6591 (2001), which is incorporated herein by reference in its entirety).

The Fc (or Fc portion of a chimeric polypeptide) can be at least about 60%, about 70%, about 80%, about 90%, about 95%, about 96%, about 97%, about 98%, about 99%, or about 100% identical to the Fc amino acid sequence shown in Table 14 (e.g., amino acids 21 to 247 of SEQ ID NO: 4). The Fc (or Fc portion of a chimeric polypeptide) can be identical to the Fc amino acid sequence shown in Table 14 (e.g., amino acids 21 to 247 of SEQ ID NO: 4).

As discussed above, exemplary long-acting polypeptides also include FIX fused to one or more albumin polypeptides, albumin binding polypeptides, or albumin-binding small molecules. In one embodiment, the albumin is human albumin. The albumin or albumin binding protein can be fused to either the N-terminal end of FIX or to the C-terminal end of FIX or inserted between two amino acids in FIX. Examples of albumin, e.g., fragments thereof, that can be used in the present invention are known. e.g., U.S. Pat. Nos. 7,592,010; 6,686,179; and Schulte, Thrombosis Res. 124 Suppl. 2:S6-S8 (2009), each of which is incorporated herein by reference in its entirety.

The albumin binding polypeptides can compromise, without limitation, bacterial albumin-binding domains, albumin-binding peptides, or albumin-binding antibody fragments that can bind to albumin. Domain 3 from streptococcal protein G, as disclosed by Kraulis et al., FEBS Lett. 378: 190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO: 5). See, e.g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Rooverset et al., Cancer Immunol. Immunother. 56:303-317 (2007), and Holt et al., Prot. Eng. Design Sci., 21:283-288 (2008), which are incorporated herein by reference in their entireties.

In certain aspects, a recombinant FIX polypeptide of the invention comprises at least one attachment site for a non-polypeptide small molecule, variant, or derivative that can bind to albumin thereof. An example of such albumin binding moieties is 2-(3-maleimidopropanamido)-6-(4-(4-iodophenyl)butanamido)hexanoate ("Albu" tag) as disclosed by Trusselet et al., Bioconjugate Chem. 20:2286-2292 (2009).

As discussed above, exemplary long-acting polypeptides also include FIX fused to at least one C-terminal peptide (CTP) of the β subunit of human chorionic gonadotropin or fragment, variant, or derivative thereof. The CTP can be fused to FIX either the N-terminal end of FIX or to the C-terminal end of FIX. One or more CTP peptides fused to or inserted into a recombinant protein is known to increase the in vivo half-life of that protein. See, e.g., U.S. Pat. No. 5,712,122, incorporated by reference herein in its entirety. Exemplary CTP peptides include DPRFQDSSSSKAPPPSLPSPSRLPGPSDTPIL (SEQ ID NO: 6) or SSSSKAPPPSLPSPSRLPGPSDTPILPQ. (SEQ ID NO: 7). See, e.g., U.S. Patent Application Publication No. US 2009/0087411 A1, incorporated by reference.

As discussed above, exemplary long-acting polypeptides also include FIX fused to at least one PAS sequence or fragment, variant, or derivative thereof. The PAS sequence can be fused to either the N-terminal end of FIX or to the C-terminal end of FIX. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline can be selected from the group consisting of Arg, Asn, Asp, Cys, Gln, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoagulant activity.

Non-limiting examples of the PAS peptides include ASPAAPAPASPAAPAPSAPA (SEQ ID NO: 8), AAPASPA-PAAPSAPAPAAPS (SEQ ID NO: 9), APSSPSP-SAPSSPSPASPSS (SEQ ID NO: 10), APSSPSP-SAPSSPSPASPS (SEQ ID NO: 11), SSPSAPSPSSPASPSPSSPA (SEQ ID NO: 12), AASPAAP-SAPPAAASPAAPSAPPA (SEQ ID NO: 13), ASAAAPAAASAAASAPSAAA (SEQ ID NO: 14) or any variants, derivatives, fragments, or combinations thereof. Additional examples of PAS sequences are known from, e.g., US Pat. Publ. No. 2010/0292130 A1, PCT Appl. Publ. No. WO 2008/155134 A1, and European issued patent EP2173890.

As discussed above, exemplary long-acting polypeptides also include FIX fused to at least one transferrin peptide or fragment, variant, or derivative thereof. At least one transferrin peptide can be fused to either the N-terminal end of FIX or to the C-terminal end of FIX or inserted between two amino acids in FIX. Any transferrin can be fused to or inserted into a recombinant FIX protein of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and 595936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., *Trends Pharmacol. Sci.* 23:206-209 (2002)). Transferrin fusion proteins have been studied for half-life extension, targeted deliver for cancer therapies, oral delivery and sustained activation of proinsulin (Brandsma et al., *Biotechnol. Adv.*, 29: 230-238 (2011); Bai et al., *Proc. Natl. Acad. Sci. USA* 102:7292-7296 (2005); Kim et al., *J. Pharmacol. Exp. Ther.*, 334:682-692 (2010); Wang et al., *J. Controlled Release* 155:386-392 (2011)).

As discussed above, exemplary long-acting polypeptides also include FIX fused to at least one polyethylene glycol (PEG) moieties.

PEGylated FIX can refer to a conjugate formed between FIX and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 daltons. These average molecular weights are provided merely as examples and are not meant to be limiting in any way.

A recombinant long-acting FIX protein of the invention can be PEGylated to include mono- or poly-(e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326. As a non-limiting example, FIX variants can contain cysteine substitutions in one or more insertion sites in FIX, and the cysteines can be further conjugated to PEG polymer. See Mei et al., *Blood* 116:270-279 (2010) and U.S. Pat. No. 7,632,921, which are incorporated herein by reference in their entireties.

As discussed above, exemplary long-acting polypeptides also include FIX fused to at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

Factor IX coagulant activity is expresses as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

Buffering Agent

Buffering agents useful for the present invention can be a weak acid or base used to maintain the acidity (pH) of a solution near a chosen value after the addition of another acid or base. Suitable buffering agents can maximize the stability of the pharmaceutical formulations by maintaining pH control of the formulation. Suitable buffering agents can also ensure physiological compatibility or optimize solubility. Rheology, viscosity and other properties can also dependent on the pH of the formulation. Common buffering agents include, but are not limited to, histidine, citrate, succinate, acetate and phosphate. In some embodiments, a buffering agent comprises L-histidine or mixtures of L-histidine with L-histidine hydrochloride with isotonicity agents and potentially pH adjustment with an acid or a base known in the art.

In certain embodiments, the buffering agent is L-histidine. In certain embodiments, the pH of the formulation is maintained between about 6 and about 8, or between about 6.5 and about 7.5.

Stabilizing Agent

Stabilizing agents are added to a pharmaceutical product in order to stabilize that product. Such agents can stabilize proteins in a number of different ways. Common stabilizing agents include, but are not limited to, amino acids such as glycine, alanine, lysine, arginine, or threonine, carbohydrates such as glucose, sucrose, trehalose, raffinose, or maltose, polyols such as glycerol, mannitol, sorbitol, cyclodextrins or destrans of any kind and molecular weight, or PEG. In one aspect of the invention, the stabilizing agent is chosen in order to maximize the stability of FIX polypeptide in lyophilized preparations. In certain embodiments, the stabilizing agent is sucrose.

Bulking Agent

Bulking agents can be added to a pharmaceutical product in order to add volume and mass to the product, thereby facilitating precise metering and handling thereof. Common bulking agents include, but are not limited to, lactose, sucrose, glucose, mannitol, sorbitol, calcium carbonate, or magnesium stearate. In certain embodiments, the bulking agent is mannitol.

Surfactant

Surfactants are amphipathic substances with lyophilic and lyophobic groups. A surfactant can be anionic, cationic, zwitterionic, or nonionic. Examples of nonionic surfactants include, but are not limited to, alkyl ethoxylate, nonylphenol ethoxylate, amine ethoxylate, polyethylene oxide, polypropylene oxide, fatty alcohols such as cetyl alcohol or oleyl alcohol, cocamide MEA, cocamide DEA, polysorbates, or dodecyl dimethylamine oxide. In certain embodiments, the surfactant is polysorbate 20 or polysorbate 80.

Pre-Lyophilization Formulation

In one aspect, the disclosure provides a pre-lyophilization formulation comprising:
(a) a Factor IX (FIX) polypeptide having FIX coagulation activity;
(b) a buffering agent;
(c) a stabilizing agent;
(d) a bulking agent; and
(e) a surfactant,
wherein the formulation has a fill volume of less than about 5 mL, less than about 4 mL, or less than about 3 mL and wherein each of (a)-(e) are at an amount per vial (mg/vial) sufficient to allow
(1) improved stability of the FIX polypeptide when lyophilized;
(2) reduced reconstitution time when lyophilized;
(3) reduced splashing onto a stopper comprising the formulation;
(4) reduced lyophilization cycle time;
(5) increased shelf-life of a lyophilate prepared from the pre-lyophilization formulation at room temperature; or
(6) any combinations thereof,
compared to a reference pre-lyophilization formulation, and wherein the reference formulation comprises (a)-(e) at the amount per vial identical to the pre-lyophilization formulation, but has at least 5 mL fill volume. In some embodiments, the reference formulation has a 5.3 mL fill volume or a 5 mL fill volume.

In other embodiments, the pre-lyophilization formulation allows at least two, at least three, at least four, or at least five properties selected from (1) improved stability of the FIX polypeptide when lyophilized; (2) reduced reconstitution time when lyophilized; (3) reduced splashing onto a stopper comprising the formulation; (4) reduced lyophilization cycle time; and n(5) increased shelf-life of a lyophilate prepared from the pre-lyophilization formulation at room temperature. In certain embodiments, the pre-lyophilization formulation allows (1) improved stability of the FIX polypeptide when lyophilized. In certain embodiments, the pre-lyophilization formulation allows (2) reduced reconstitution time when lyophilized. In certain embodiments, the pre-lyophilization formulation allows (3) reduced splashing onto a stopper comprising the formulation. In certain embodiments, the pre-lyophilization formulation allows (4) reduced lyophilization cycle time. In certain embodiments, the pre-lyophilization formulation allows (5) increased shelf-life of a lyophilate prepared from the pre-lyophilization formulation at room temperature. In certain embodiments, the pre-lyophilization formulation allows (6) any combinations of properties described herein.

In certain embodiments, the pre-lyophilization formulation comprises at least about 100 IU/vial of the FIX polypeptide. In certain embodiments, the pre-lyophilization formulation comprises at least about 200 IU/vial to about 10,000 IU/vial of the FIX polypeptide, about 200 IU/vial to about 6,000 IU/vial, or about 500 IU/vial to about 5,000 IU/vial. In certain embodiments, the pre-lyophilization formulation comprises about 220 IU/vial, about 250 IU/vial, about 300 IU/vial, about 400 IU/vial, about 500 IU/vial, about 600 IU/vial, about 700 IU/vial, about 800 IU/vial, about 900 IU/vial, about 1,000 IU/vial, about 1,100 IU/vial, about 1,200 IU/vial, about 1,300 IU/vial, about 1,400 IU/vial, about 1,500 IU/vial, about 2,000 IU/vial, about 2,500 IU/vial, about 3,000 IU/vial, about 4,000 IU/vial, about 5,000 IU/vial, about 5,500 IU/vial, about 6,000 IU/vial, about 6,500 IU/vial, about 7,000 IU/vial, about 7,500 IU/vial, about 8,000 IU/vial, about 8,500 IU/vial, about 9,000 IU/vial, about 9,500 IU/vial or about 10,000 IU/vial of the FIX polypeptide.

In some embodiments, a higher concentration of the pre-lyophilization formulation is achieved by reducing the fill volume. In certain embodiments, the pre-lyophilization formulation has the fill volume of about 4.0 mL, about 3.5 mL, about 3.0 mL, about 2.9 mL, about 2.8 mL, about 2.7 mL, about 2.65 mL, about 2.6 mL, about 2.5 mL, about 2.4 mL, about 2.3 mL, about 2.2 mL, about 2.1 mL, or about 2.0 mL. In some embodiments, the fill volume of the pre-lyophilization formulation is about 2.65 mL. In some embodiments, the fill volume of the pre-lyophilization formulation is less than about 5 mL.

In some embodiments, the FIX polypeptide can be further concentrated by an additional purification step, e.g., a second ultra filtration step.

In certain embodiments, the reduced reconstitution time is less than 1.5 minute, less than 1 minute, less than 50 seconds, less than 40 seconds, less than 30 seconds, less than 20 seconds, or less than 10 seconds. In specific embodiments, the reduced reconstitution time is less than 30 seconds.

In certain embodiments, the reduced lyophilization cycle time of the pre-lyophilization formulation is about 4 days or less, about 3 days or less, about 2 days or less, or about a day or less.

In certain embodiments, the concentration of the buffering agent in the pre-lyophilization formulation is between about 3 mg/mL and about 15 mg/mL, between 4 mg/mL and between 12 mg/mL, between about 5 mg/mL and about 10 mg/mL, or between about 5.82 mg/mL and about 9.7 mg/mL. In one embodiment, the buffering agent is at a concentration of between about 3.88 mg/mL and about 9.7 mg/mL. In one embodiment, the buffering agent is at a concentration of about 7.76 mg/mL. In some embodiments, the pre-lyophilization formulation contains L-histidine at a concentration of about 7.76 mg/mL.

In certain embodiments, the concentration of the stabilizing agent in the pre-lyophilization formulation is between 10 mg/mL and about 50 mg/mL, between about 13 mg/mL and about 40 mg/mL, between about 15 mg/mL and about 35 mg/mL, or between about 17.85 mg/mL and about 29.95 mg/mL. In one embodiment, the buffering agent is at a concentration of about 23.8 mg/mL. In some embodiments, the pre-lyophilization formulation contains sucrose at a concentration of 23.8 mg/mL.

In certain embodiments, the concentration of the bulking agent in the pre-lyophilization formulation is between about 20 mg/mL and about 100 mg/mL, between about 30 mg/mL and about 70 mg/mL, between about 30 mg/mL and about 60 mg/mL, or between about 35.7 mg/mL and about 59.5 mg/mL. In one embodiment, the bulking agent is at a concentration of about 47.6 mg/mL. In some embodiments, the pre-lyophilization formulation contains mannitol at a concentration of about 47.6 mg/mL.

In certain embodiments, the concentration of the surfactant in the pre-lyophilization formulation is between about 0.01 mg/mL and about 5 mg/mL, between about 0.1 mg/mL and about 4 mg/mL, between about 0.1 mg/mL and about 3 mg/mL, between about 0.01 mg/mL and about 2 mg/mL, or between about 0.05 mg/mL and about 1 mg/mL. In one embodiment, the surfactant is at a concentration of about 0.2 mg/mL. In some embodiments, the pre-lyophilization formulation contains polysorbate 20 or polysorbate 80 at a concentration of about 0.2 mg/mL.

In certain embodiments, the concentration of the FIX polypeptide in the pre-lyophilization formulation is between about 80 IU/mL and about 2,750 IU/mL. In some embodiments, the concentration of the FIX polypeptide in the pre-lyophilization formulation is at least about 100 IU/mL, at least about 200 IU/mL, at least about 300 IU/mL, at least about 400 IU/mL, at least about 500 IU/mL, at least about 600 IU/mL, at least about 700 IU/mL, at least about 800 IU/mL, at least about 900 IU/mL, at least about 1000 IU/mL, at least about 1500 IU/mL, at least about 2000 IU/mL, or at least about 2500 IU/mL.

In one aspect, the disclosure further provides a pre-lyophilization formulation comprising:
(a) about 80 to about 2,750 IU/mL of rFIXFc;
(b) about 7.76 mg/mL of L-histidine.
(c) about 47.6 mg/mL of mannitol;
(d) about 23.8 mg/mL of sucrose; and,
(e) about 0.2 mg/mL of polysorbate-20.

In certain embodiments, the fill volume of such pre-lyophilization formulation is about 3 mL, about 2.9 mL, about 2.8 mL, about 2.7 mL, about 2.65 mL, about 2.6 mL, about 2.5 mL, about 2.4 mL, about 2.3 mL, about 2.2 mL, about 2.1 mL, or about 2.0 mL. In one embodiment, the fill volume of such pre-lyophilization formulation is about 2.65 mL.

In addition, this disclosure provides a lyophilate powder which is lyophilized from any of the above pre-lyophilization formulations. In some embodiments, the pre-lyophilization formulation is any formulation described herein.

Lyophilate Power

The disclosure also provides a lyophilate powder comprising a FIX polypeptide, a buffering agent, a stabilizing agent, a bulking agent, a surfactant, or any combinations thereof.

In certain embodiments, the lyophilate powder comprises between about 8 mg and about 39 mg per vial, between about 9 mg and about 35 mg per vial, between about 10 mg and about 30 mg per vial, between about 12 mg and about 25 mg per vial, between about 15 mg and about 23 mg per vial of the buffering agent (e.g., L-histidine). In one embodiment, the lyophilate powder comprises about 25 mg per vial, about 24 mg per vial, about 23 mg per vial, about 22 mg per vial, about 21 mg per vial, about 20 mg per vial, about 19 mg per vial, about 18 mg per vial, about 17 mg per vial, about 16 mg per vial, about 15 mg per vial of the buffering agent. In another embodiment, the lyophilate powder comprises about 20.6 mg per vial of the buffering agent. In some embodiments, the buffering agent is L-histidine.

In certain embodiments, the lyophilate powder comprises between about 27 mg and about 132 mg per vial, between about 30 mg and about 120 mg per vial, between about 40 mg and about 110 mg per vial, between about 50 mg and about 100 mg per vial, between about 60 mg and about 90 mg per vial of the stabilizing agent. In one embodiment, the lyophilate powder comprises about 68 mg per vial, about 67 mg per vial about 66 mg per vial about 65 mg per vial about 64 mg per vial about 63 mg per vial about 62 mg per vial about 61 mg per vial about 60 mg per vial about 59 mg per vial of the stabilizing agent. In another embodiment, the lyophilate power comprises about 63.1 mg per vial of the stabilizing agent. In some embodiments, the stabilizing agent is sucrose.

In certain embodiments, the lyophilate powder comprises between about 50 mg and about 265 mg per vial, between about 53 mg and about 265 mg per vial, between about 50 mg and about 250 mg per vial, between about 53 mg and about 265 mg per vial, between about 80 mg and about 200 mg per vial, between about 100 mg and about 150 mg per vial, or between about 110 mg and about 140 mg per vial of the bulking agent. In one embodiment, the lyophilate powder comprises about 131 mg per vial, about 130 mg per vial, about 129 mg per vial, about 128 mg per vial, about 127 mg per vial, about 126 mg per vial, about 125 mg per vial, about 124 mg per vial, about 123 mg per vial, or about 122 mg per vial of the bulking agent. In another embodiment, the lyophilate powder comprises about 126.1 mg per vial of the bulking agent. In some embodiments, the bulking agent is mannitol.

In certain embodiments, the lyophilate powder comprises between about 0.03 mg and about 13 mg per vial, between about 0.05 mg and about 10 mg per vial between about 0.07 mg and about 8 mg per vial between about 0.1 mg and about 2 mg per vial of the surfactant. In one embodiment, the lyophilate powder comprises about 1 mg per vial, about 0.9 mg per vial, about 0.8 mg per vial, about 0.7 mg per vial, about 0.6 mg per vial, about 0.5 mg per vial, about 0.4 mg per vial, about 0.3 mg per vial, about 0.2 mg per vial, or about 0.1 mg per vial of the surfactant. In another embodiment, the lyophilate power comprises about 0.5 mg per vial of the surfactant. In one embodiment, the lyophilate powder comprises about 0.53 mg per vial of the surfactant. In some embodiments, the surfactant is polysorbate 20 or polysorbate 80.

In certain embodiments, the lyophilate powder comprises:
(a) a FIX polypeptide at an amount between about 2 mg per vial and about 150 mg per vial;
(b) a buffering agent at an amount between about 10 mg per vial and about 30 mg per vial;
(c) a bulking agent at an amount between about 70 mg vial and about 200 mg per vial.

(d) a stabilizing agent at an amount between about 30 mg per vial and 100 mg per vial; and
(e) a surfactant at an amount between about 0.05 mg per vial and about 5 mg per vial.

In some embodiments, the lyophilate powder comprises:
(a) a FIX polypeptide at an amount between about 2.2 mg per vial and about 125 mg per vial;
(b) a buffering agent at an amount between about 8 mg per vial and about 39 mg per vial;
(c) a bulking agent at an amount between about 53 mg vial and about 265 mg per vial.
(d) a stabilizing agent at an amount between about 27 mg per vial and 132 mg per vial; and
(e) a surfactant at an amount between about 0.03 mg per vial and about 13 mg per vial.

In certain embodiments, the lyophilate powder comprises:
(a) the lyophilized FIX polypeptide at an amount between about 2.2 mg per vial and about 125 mg per vial;
(b) the buffering agent at an amount between about 12.5 mg per vial and 25 mg per vial;
(c) the stabilizing agent at an amount between about 32.5 mg per vial and 80 mg per vial;
(d) the bulking agent at an amount between about 75 mg per vial and 150 mg per vial; and
(e) the surfactant at an amount between about 0.1 mg/mL and about 2 mg/mL.

In one embodiment, the lyophilate powder comprises:
(a) about 2.2 to about 125 mg/vial of the FIX polypeptide;
(b) about 20.6 mg/vial of L-histidine;
(c) about 126.1 mg/vial of mannitol;
(d) about 63.1 mg/vial of sucrose; and
(e) about 0.53 mg/vial of polysorbate 20.

Reconstituted Formulation

Furthermore, this disclosure provides a reconstituted formulation comprising any of the above lyophilate powder reconstituted by a reconstitution buffer.

In certain embodiments, the reconstitution buffer is a NaCl solution. In some embodiments, the reconstitution buffer is 5 mL.

In certain embodiments, the reconstituted formulation comprises:
(a) the FIX polypeptide at a concentration between about 0.9 mg/mL and about 50 mg/mL;
(b) the buffering agent at a concentration between 2 mg/mL and about 5 mg/mL;
(c) the bulking agent at a concentration between 20 mg/mL and about 30 mg/mL;
(d) the stabilizing agent at a concentration between 8 mg/mL and 15 mg/mL per vial; and
(e) the surfactant at a concentration between 0.05 mg/mL and about 0.4 mg/mL.

In certain embodiments, the reconstituted formulation comprises:
(a) the FIX polypeptide at a concentration between about 0.9 mg/mL and about 50 mg/mL;
(b) the buffering agent at a concentration of about 3.88 mg/mL;
(c) the bulking agent at a concentration of about 23.8 mg/mL;
(d) the stabilizing agent at a concentration of about 11.9 mg/mL;
(e) the surfactant at a concentration of about 0.1 mg/mL; and (0 the reconstitution buffer comprising about 3.25 mg/mL NaCl.

In certain embodiments, the reconstituted formulation comprises:
(a) the FIX polypeptide at a concentration between about 80 IU/mL and about 2,750 IU/mL;
(b) the buffering agent at a concentration of about 25 mM;
(c) the bulking agent at a concentration of about 131 mM;
(d) the stabilizing agent at a concentration of about 35 mM;
(e) the surfactant at a concentration of 0.01% (w/v); and
(0 the reconstitution buffer.

Examples of the formulation compositions are further provided in Tables 2-4.

In one aspect, the disclosure further provides a vial comprising the pre-lyophilization formulations, the lyophilate powder, or the reconstituted formulations described herein.

In another aspect, the disclosure provides a kit comprising a first container comprising the lyophilate powder described herein and a second container comprising a reconstitution buffer at a volume sufficient to produce a reconstituted formulation, when combined with the lyophilate powder of the first container. In certain embodiments, the volume of the reconstitution buffer in the kit is about 5 mL. In some embodiments, the volume is about 5.3 mL. In certain embodiments, the reconstitution buffer of the kit comprises NaCl. In some embodiments, the kit is used to treat hemophilia B.

In yet another aspect, the disclosure provides a method of administering a FIX polypeptide to a hemophilia B patient in need thereof, comprising administering to the patient the reconstituted formulation described herein, wherein the administration prevents or reduces the frequency or severity of bleeding episodes in the patient.

The disclosure further provides a method of preventing, treating, ameliorating, or managing hemophilia B in a patient in need thereof by administering the reconstituted formulation described herein.

Methods of Producing a Lyophilate Powder Comprising a FIX Polypeptide

This disclosure provides methods of producing a lyophilate powder comprising a FIX polypeptide. In one aspect, the disclosure provides lyophilization methods comprising lyophilizing the pre-lyophilization formulations described herein. In another aspect, the disclosure provides a lyophilization method comprising a single drying step.

In one aspect, this disclosure provides a method of lyophilizing a FIX polypeptide comprising:
(a) a "freezing step" comprising freezing a pre-lyophilization formulation comprising the FIX polypeptide and an aqueous solvent;
(b) a "vacuum step" comprising reducing the pressure of the frozen pre-lyophilization formulation by an amount effective to remove the aqueous solvent from the frozen pre-lyophilization formulation; and,
(c) a single "drying step" comprising increasing the temperature of the frozen pre-lyophilization formulation above the collapse temperature, thereby producing a lyophilate powder. In another aspect, the lyophilization process time is reduced compared to a reference method, e.g., lyophilization process having two or more drying steps.

In other aspects, the lyophilate power produced by the present method has one or more characteristics of the following: (1) improved stability of the FIX polypeptide; (2) reduced reconstitution time; (3) reduced splashing onto a stopper comprising the formulation; or (4) increased shelf-life of the lyophilate powder at room temperature.

In certain embodiments, the collapse temperature is −1.5° C.

In certain embodiments, the pre-lyophilization formulation is frozen to a freezing temperature of about −65 to about −40° C., about −65 to about −45° C., about −65 to about −55° C., about −60 to about −40° C., about −60 to about −50° C. or about −60 to about −55° C. during the freezing step. In certain embodiments, the pre-lyophilization formulation is frozen to a freezing temperature of about −55° C. during the freezing step. In certain embodiments, the freezing temperature is ramped down from about 5° C. to about −55° C. during the freezing step.

In certain embodiments, the freezing temperature is held from about 30 minutes to about 5 hours, about 1 hour to about 5 hours, about 1.5 hours to about 5 hours, about 1.5 hours to about 4 hours, about 1.5 hours to about 3 hours, or about 1.5 hours to about 2.5 hours during the freezing step. In certain embodiments, the freezing temperature is held for about 2 hours during the freezing step.

In certain embodiments, the frozen pre-lyophilization formulation of step (a) is further subject to an "annealing step" (a') prior to the "vacuum step" (b). In certain embodiments, the temperature of the frozen pre-lyophilization formulation of step (a) is ramped up to an annealing temperature of about −15° C. to about −2° C. during the annealing step. In certain embodiments, the temperature of the frozen pre-lyophilization formulation of step (a) is ramped up to an annealing temperature of about −6° C. during the annealing step.

In certain embodiments, the annealing temperature is held for about 2 hours to about 4 hours during the annealing step. In certain embodiments, the annealing temperature is held for about 30 minutes to about 5 hours, about 1 hour to about 5 hours, about 2 hours to about 5 hours, about 2 hours to about 4 hours or about 2.5 hours to about 3.5 hours during the annealing step. In certain embodiments, the annealing temperature is held for about 3 hours during the annealing step.

In certain embodiments, the temperature of the frozen pre-lyophilization formulation is ramped down from the annealing temperature to a temperature of about −65° C. to about −40° C. during the annealing step. In certain embodiments, the temperature of the frozen pre-lyophilization formulation is ramped down from the annealing temperature to a temperature of −55° C. during the annealing step.

In certain embodiments, the "vacuum step" comprises subjecting the frozen pre-lyophilization formulation to a vacuum between about 0.05 and about 1 mbar, between about 0.05 and about 0.50 mbar, between about 0.10 and about 0.50 mbar, between about 0.15 and about 0.50 mbar, between about 0.20 and about 0.50 mbar, or between about 0.25 and about 0.50 mbar. In certain embodiments, the vacuum in the "vacuum step" is about 0.33 mbar.

In certain embodiments, the vacuum is held in the "vacuum step" for about 5 hours, about 4 hours, about 3 hours, about 2 hours, or about 1 hour. In some embodiments, the vacuum is held in the "vacuum step" for about 2 hours.

In certain embodiments, the "drying step" comprises ramping up the temperature of the frozen pre-lyophilization formulation from about −55° C. to a drying temperature of about 40° C. In certain embodiments, the drying temperature is at least about 30° C., at least about 32° C., at least about 34° C., at least about 35° C., at least about 36° C., at least about 38° C., at least about 39° C., at least about 40° C. In other embodiments, the drying temperature is about 35° C., about 40° C., about 32° C., or about 45° C.

In certain embodiments, the drying step further comprises holding the drying temperature for about 10 hours to about 40 hours, about 10 hours to about 30 hours, or about 20 hours to about 30 hours. In certain embodiments, the drying temperature is held for about 25 hours.

In certain embodiments, the drying step is carried out at a pressure of about 0.05 mbar to about 1 mbar, between about 0.05 and about 0.50 mbar, between about 0.10 and about 0.50 mbar, between about 0.15 and about 0.50 mbar, between about 0.20 and about 0.50 mbar, or about 0.20 mbar to about 0.45 mbar. In certain embodiments, the pressure is held at about 0.33 mbar during the drying step. The unit of mbar can be converted to Torr or any other units. For example, 1 mbar can be converted to 0.75006375541921 Torr.

In one aspect, the disclosure provides a method of producing a lyophilate powder comprising a FIX polypeptide, comprising:
- (a) a "freezing step" comprising freezing a pre-lyophilization formulation comprising a FIX polypeptide by ramping down the temperature for about 2 hours to a freezing temperature of about −55° C., and holding the freezing temperature for about 2 hours;
- (a') an "annealing step" comprising ramping up for about 1.5 hours the temperature of the frozen pre-lyophilization formulation of step (a) to an annealing temperature of about −6° C., holding the annealing temperature for about 3 hours, and ramping down the temperature for about 1.5 hours to about −55° C.;
- (b) a "vacuum step" comprising holding the frozen pre-lyophilization formulation of step (a') at about −55° C. for two hours at atmospheric pressure and ramping down the pressure for about 2 hours to about 0.33 mbar; and,
- (c) a single "drying step" comprising ramping up for 3 hours the temperature of the frozen pre-lyophilization formulation of step (b) to about 40° C., while holding the pressure at about 0.33 mbar, and holding the temperature of the frozen pre-lyophilization formulation at about 40° C. for about 25 hours, while holding the pressure at about 0.33 mbar, thereby producing the lyophilate powder. In some embodiments, the lyophilization method takes less cycle time.

In certain embodiments, the lyophilate powder produced by the methods described herein has the following characteristics:
- (1) improved stability of the FIX polypeptide;
- (2) reduced reconstitution time;
- (3) reduced splashing onto a stopper comprising the formulation;
- (4) increased shelf-life of the lyophilate powder at room temperature; or
- (5) any combinations thereof, In some embodiments, the lyophilization cycle period can be less than about 4.5 days, about 4 days, about 3.5 days, about 3 days, about 2.5 days, or about 2 days. In other embodiments, the lyophilization cycle period is about 3 days or less. In certain embodiments, the fill volume of the pre-lyophilization formulation used in the lyophilization method is less than about 5 mL. In certain embodiments, the fill volume is about 4 mL, about 3.5 mL, about 3.0 mL, about 2.9 mL, about 2.8 mL, about 2.7 mL, about 2.65 mL, about 2.6 mL, about 2.5 mL, about 2.4 mL, about 2.3 mL, about 2.2 mL, about 2.1 mL, or about 2.0 mL. In one embodiment, the fill volume is about 2.65 mL.

In certain embodiments, the reduced reconstitution time of the lyophilate powder produced by the lyophilization method is less than about 1.5 minutes, less than about 1 minute, less than about 50 seconds, less than about 40 seconds, less than about 30 seconds, less than about 20 seconds, or less than about 10 seconds. In certain embodiments, the reduced reconstitution time of the lyophilate powder produced by the lyophilization method is less than about 30 seconds.

In certain embodiments, the reduced lyophilization cycle time of the pre-lyophilization formulation used in the lyophilization method is about 4 days or less, about 3 days or less, about 2 days or less, or about a day or less.

In some embodiments, the lyophilate powder is produced from the pre-lyophilization formulation in about 90 hours or less, about 80 hours or less, about 70 hours or less, about 60 hours or less, about 50 hours or less, about 45 hours or less, about 40 hours or less, or about 30 hours or less. In certain embodiments, the lyophilate powder is produced from the pre-lyophilization formulation in about 45 hours or less.

In certain embodiments, the residual moisture in the lyophilate powder is less than about 1.0%, about 0.7%, about 0.6%, about 0.5%, about 0.4% or about 0.3%. In some embodiments, the residual moisture in the lyophilate powder is less than about 0.5%.

In one aspect, the disclosure provides a method of stabilizing a lyophilate powder comprising a FIX polypeptide, comprising lyophilizing a pre-lyophilization formulation according to the methods described herein, wherein the lyophilate powder is stabilized as measured by Size Exclusion Chromatography (SEC) with respect to a lyophilate powder prepared by using a lyophilization method comprising more than one drying step.

In another aspect, the disclosure provides a method of increasing the shelf-life of a lyophilate powder comprising a FIX polypeptide, comprising lyophilizing a pre-lyophilization formulation according to the methods described herein, wherein the shelf-life of the lyophilate powder is increased as measured by SEC and/or FIX clotting activity assay with respect to the shelf-life of a lyophilate powder prepared by using a lyophilization method comprising more than one drying step.

This disclosure also provides a method to decrease the reconstitution time of a lyophilate powder comprising a FIX polypeptide, comprising lyophilizing a pre-lyophilization formulation according to the methods described herein, wherein the reconstitution time of the lyophilate powder is decreased with respect to the reconstitution time of a lyophilate powder prepared by using a lyophilization method comprising more than one drying step.

This disclosure further provides a method to reduce lyophilization process time of producing a lyophilate powder comprising a FIX polypeptide, comprising lyophilizing a pre-lyophilization formulation according to the methods described herein, wherein the lyophilization process time of the pre-lyophilization formulation is reduced with respect to the lyophilization process time of producing a lyophilate powder using a lyophilization method comprising more than one drying step.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1: Factor IX-Fc Drug Substance and Drug Product Compositions rFIXFc Description rFIXFc is a long-acting, fully recombinant fusion protein consisting of human coagulation Factor IX (FIX) covalently linked to the Fc domain of human immunoglobulin G1 (IgG1). The Factor IX portion of rFIXFc has a primary amino acid sequence that is identical to the $Thr^{148}$ allelic form of plasma derived Factor IX and has structural and functional characteristics similar to endogenous Factor IX, The Fc domain of rFIXFc contains the hinge, CH2 and CH3 regions of IgG1. rFIXFc contains 869 amino acids with a molecular weight of approximately 98 kilodaltons.

rFIXFc is produced by recombinant DNA technology in a human embryonic kidney (HEK) cell line and then purified.

The rFIXFc drug product formulation of the invention comprising rFIXFc can allow development of high concentration drug products, e.g., 4000+IU/vial drug product strengths. This requires a higher concentration of rFIXFc protein in the drug substance, as shown in the comparison Table 1 below. The rFIXFc drug product formulation of the invention can increase the shelf life of the 250 & 500 IU/vial drug product strengths to allow increased room temperature stability. Development data suggests that the 250 and 500 IU/vial drug product strengths are significantly more stable under accelerated conditions than the reference drug product.

The rFIXFc drug product formulation of the invention can also decrease the reconstitution time when lyophilized. Reference drug product reconstitution time varies between 1-2 minutes. Development data suggests that the LCM drug product reduces the reconstitution time to less than 30 seconds.

The rFIXFc drug product formulation of the invention can also allow reduction of the lyophilization process time. Currently the lyophilization cycle is ~4.5 days. With a lower vial fill volume this can likely be reduced to ~3 days or less for more economical manufacturing.

Drug Substance (DS)

The drug substance for the rFIXFc formulation of the invention will use the same formulation excipients as the reference drug substance. The higher concentration will be achieved using a second ultrafiltration step during drug substance manufacturing. See Table 1.

TABLE 1

| Drug Substance Compositions | | |
| --- | --- | --- |
| Component | Reference Drug Product | Drug Product |
| rFactorIX-Fc | 10-13 mg/mL | 65-75 mg/mL |
| L-Histidine | 3.88 mg/mL (25 mM) | 3.88 mg/mL (25 mM) |
| Polysorbate 20 | 0.1 mg/mL (0.01%) | 0.1 mg/mL (0.1%) |

Drug Product (DP)

In order to accomplish the objectives stated above, a drug product was designed that doubled the concentrations of all components of the reference drug product (protein & excipients), while reducing the fill volume of the vial prior to lyophilization. This ensures that the dose of all components to the patient remains constant, while improving the drug product performance parameters mentioned above.

Tables 2-4 below detail the composition of the lyophilization feedstock, the contents of the solid product in the vial after lyophilization and the composition after reconstitution. It is important to note the wide variance of the rFIXFc protein concentrations. Due to the fact that each batch of Factor IX is slightly different in its activity in IU/mg, the feedstock is compounded using the assayed activity. This results in a range of protein concentrations, and this variance added to the different strengths of drug products gives the ranges stated below.

TABLE 2

Drug Product - Pre-lyophilization Formulation Compositions
Drug Product Lyophilization Feedstock Compositions

| Component | Reference Drug Product 250-2000 IU/Vial | Reference Drug Product 3000 IU/Vial | Drug Product 250-5500 IU/Vial |
|---|---|---|---|
| rFactorIX-Fc | 0.45-9.5 mg/mL 40-500 IU/mL | 5.5-13.7 mg/mL 480-750 IU/mL | 0.9-50 mg/mL 80-2750 IU/mL |
| L-Histidine | 3.88 mg/mL (25 mM) | 3.88 mg/mL (25 mM) | 7.76 mg/mL (50 mM) |
| Mannitol | 23.8 mg/mL (131 mM) | 23.8 mg/mL (131 mM) | 47.6 mg/mL (261 mM) |
| Sucrose | 11.9 mg/mL (35 mM) | 11.9 mg/mL (35 mM) | 23.8 mg/mL (70 mM) |
| Polysorbate 20 | 0.1 mg/mL (0.01%) | 0.1 mg/mL (0.01%) | 0.2 mg/mL (0.2%) |
| Feedstock Fill Volume | 5.3 mL | 7.4 mL | 2.65 mL |

TABLE 3

Drug Product - Lyophilate Compositions
Drug Product Lyophilized Vial Solid Compositions

| Component | Reference Drug Product 250-2000 IU/Vial | Reference Drug Product 3000 IU/Vial | Drug Product 250-5500 IU/Vial* |
|---|---|---|---|
| rFactorIX-Fc | 2.2-46 mg/vial | 28-69 mg/vial | 2.2-125 mg/vial |
| L-Histidine | 19.4 mg/vial | 27.2 mg/vial | 19.4 mg/vial |
| Mannitol | 119 mg/vial | 167 mg/vial | 119 mg/vial |
| Sucrose | 59.5 mg/vial | 83.3 mg/vial | 59.5 mg/vial |
| Polysorbate 20 | 0.5 mg/vial | 0.7 mg/vial | 0.5 mg/vial |

*The values are the nominal values that do not include the overfill. The values including the overfill are: 20.6 mg/vial (L-histidine), 126.01 mg/vial (mannitol), 63.1 mg/vial (sucrose), and 0.53 mg/vial (polysorbate).

TABLE 4

Drug Product - Reconstituted Formulation Compositions
Post-Reconstitution Drug Product Vial Compositions

| Component | Reference Drug Product 250-2000 IU/Vial | Reference Drug Product 3000 IU/Vial | Drug Product 250-5500 IU/Vial |
|---|---|---|---|
| Diluent | 5.2 mL of NaCl in Water for Injection | | |
| rFactorIX-Fc | 0.45-9.5 mg/mL 40-500 IU/mL | 5.5-13.7 mg/mL 480-750 IU/mL | 0.9-50.0 mg/mL 80-2750 IU/mL |
| L-Histidine | 3.88 mg/mL (25 mM) | 5.43 mg/mL (35 mM) | 3.88 mg/mL (25 mM) |
| Mannitol | 23.8 mg/mL (131 mM) | 33.3 mg/mL (183 mM) | 23.8 mg/mL (131 mM) |
| Sucrose | 11.9 mg/mL (35 mM) | 16.7 mg/mL (48 mM) | 11.9 mg/mL (35 mM) |
| Polysorbate 20 | 0.1 mg/mL (0.01%) | 0.14 mg/mL (0.014%) | 0.1 mg/mL (0.01%) |

TABLE 4-continued

Drug Product - Reconstituted Formulation Compositions
Post-Reconstitution Drug Product Vial Compositions

| Component | Reference Drug Product 250-2000 IU/Vial | Reference Drug Product 3000 IU/Vial | Drug Product 250-5500 IU/Vial |
|---|---|---|---|
| Reconstitution buffer | 3.25 mg/mL | 3.25 mg/mL | 3.25 mg/mL |
| Reconstituted Volume | 5.3 mL | 5.3 mL | 5.3 mL |

Example 2: Development of Lyophilization Cycle Parameters for the Second Generation rFIXFc Drug Product Summary The goal of this study was to evaluate ranges around the drying phase process parameters of the lyophilization cycle for the rFIXFc drug product of the invention.

This report summarizes a statistical design of experiments (DOE) study evaluating the lyophilization process parameters (Drying Shelf Temperature, Chamber Vacuum Level and Drying Time) and their effect on the product temperature during drying, the resulting residual moisture and drying rate of the drug product.

Preliminary lyophilization cycle design experiments on the Second Generation rFIXFc drug product demonstrated that distinct primary and secondary drying steps were not necessary due to the formulation's high collapse temperature of approximately −1.5° C. A 12 experiment Design of Experiments (DOE) study was developed to evaluate the effect of the shelf temperature, vacuum level and drying time on the residual moisture levels and product temperatures during the lyophilization process on the placebo. An analysis of the data shows that in order to achieve a residual moisture level below 1%, a minimum shelf temperature of 30° C. during the drying phase is required. The analysis also demonstrated that drying times longer than 25 hours do not further decrease the residual moisture in the vials, and the chamber vacuum level has only a small effect on the residual moisture. The product temperatures during drying are significantly affected by the shelf temperature and chamber vacuum level, but the most aggressive drying conditions in the study (40° C. Shelf Temperature at 1000 mTorr Chamber Vacuum) resulted in a product temperature that was more than 10° C. colder than the collapse temperature. The vial mass flow is predominantly a function of the shelf temperature, and in order to maintain vacuum control, the commercial lyophilizer will need to be able to handle moisture flow rates of 0.7 g/hr/vial. A lyophilization cycle was proposed to achieve product with <0.5% residual moisture using a shelf temperature of 40° C., a chamber vacuum of 250 mTorr (0.33 mBar) and a drying time of 25 hours.

Introduction

The Second Generation FactorIX-Fc (rFIXFc-2G) Drug Product composition was designed to allow for improved protein stability during accelerated storage, improved reconstitution time, and reduced fill volume to reduce splashing onto the stoppers. This was accomplished by reducing the fill volume from 5.3 mL to 2.65 mL, and doubling the concentrations of protein and excipients in the formulation such that the reconstituted product is the same as the first generation composition. Another benefit to reducing the fill volume was a decrease in the amount of water that needs to be removed during the lyophilization process.

Since the new drug product design required revalidation of the drug product process, the lyophilization cycle was redeveloped. The collapse temperature of the placebo formulation was measured as approximately −1.5° C., which would allow a shorter lyophilization cycle to be used than was designed for the reference rFIXFc lyophilization process. It was determined through initial experiments that no separate primary drying step was required, as the product did not undergo collapse even at shelf temperatures in excess of 40° C. A cycle was designed using the freezing profile from the reference drug product combined with a direct step to the primary drying temperature after vacuum is applied. The placebo is a good surrogate for active rFIXFc-2G vials since the mannitol provides the crystalline structure for the cake making the appearance the same as the active vials. Amorphous sugar is also more difficult to dry than protein, so the resulting residual moisture is slightly higher, providing a worst-case value for the process. Removal of the protein from the vials also reduces the resistance to water vapor, giving a worst case estimate for the vial mass flow rate.

A statistical design of experiments (DOE) study was carried out to evaluate the lyophilization process parameters (Drying Shelf Temperature, Chamber Vacuum Level and Drying Time) and their effect on the product temperature during the drying process, the resulting residual moisture, and drying rate of the drug product.

Materials and Methods

The goal of this study was to evaluate ranges around the drying phase process parameters of the lyophilization cycle for the second generation rFIXFc drug product. The drying phase parameters and ranges used to design the DOE study in JMP 9 are shown in Table 5. The resulting 12 experiment DOE plan showing the individual run parameter setpoints is shown in Table 6.

TABLE 5

The Drying Parameter Ranges Used in the DOE Study Design

| Drying DOE Parameter | Minimum Value | Maximum Value |
| --- | --- | --- |
| Shelf Temperature (° C.) | 0 | 40 |
| Chamber Vacuum (mTorr) | 100 | 1000 |
| Drying Time (h) | 15 | 35 |

TABLE 6

The Study Design of Experiments Template Output from JMP 9

| Run | Temp (C.) | Vacuum (mT) | Time (hr) |
| --- | --- | --- | --- |
| 1 | 40 | 100 | 35 |
| 2 | 0 | 100 | 15 |
| 3 | 40 | 1000 | 25 |
| 4 | 20 | 100 | 28.2 |
| 5 | 20 | 500 | 25 |
| 6 | 0 | 100 | 25 |
| 7 | 20 | 550 | 25 |
| 8 | 40 | 250 | 15 |
| 9 | 20 | 1000 | 15 |
| 10 | 0 | 1000 | 35 |
| 11 | 10 | 500 | 25 |
| 12 | 40 | 500 | 25 |

For each lyophilization cycle in the study, eighty 10 mL Schott vials (P/N: 68000320) were filled with 2.75 mL of Second Generation rFIXFc Placebo as shown in Table 7, which provides a worst case fill volume for residual moisture evaluation. The filled vials were arranged on a single shelf with three thermocouples for each experiment as shown in FIG. 1.

TABLE 7

Second Generation rFIXFc Drug Product Placebo Recipe

| Component | FW | g/L | mM | % (w/v) |
| --- | --- | --- | --- | --- |
| Histidine | 155.15 | 7.76 | 50.00 | 0.776 |
| PS-20 | 1227.54 | 0.2 | 0.1629 | 0.020 |
| Mannitol | 182.172 | 47.6 | 261.29 | 4.760 |
| Sucrose | 342.30 | 23.8 | 69.53 | 2.380 |
| | ρ= | 1.029 | g/mL | |

The lyophilization cycles used were variations of the cycle shown in Table 8. The Lyophilizer Shelf Drying Temperature, Drying Step Time and Drying Vacuum Level were varied based on the Design of Experiments table shown in Table 6. An SP Industries Lyostar II was used for each lyophilization cycle, and the vials were placed on the middle shelf

TABLE 8

Lyophilization Cycle Parameters Showing the DOE Inputs of Temperature, Time and Vacuum

| Phase | Step | Temp (° C.) | Ramp (° C./min) | Soak (min) | Vacuum (mTorr) |
| --- | --- | --- | --- | --- | --- |
| Load | Load | 25 | — | As Needed | — |
| Freeze | Equilibrate | 0 | 0.5 | 60 | — |
| | Freeze | −55 | 0.5 | 120 | — |
| | Anneal | −6 | 0.5 | 180 | — |
| | Freeze | −55 | 0.5 | 120 | — |
| Pulldown | Initial Vac | −55 | — | — | DOE Vacuum |
| Drying | 1°/2° Drying | DOE Temp | Direct Step | DOE Time | DOE Vacuum |
| Final | Final | 5 | 5.0 | As Needed | DOE Vacuum |

After each lyophilization cycle, five vials were selected from corner and middle positions and measured for residual moisture using procedure TDMP-74, and averaged over the shelf. The product temperature during drying and the vial mass flow rate were measured using thermocouples and by Manometric Temperature Measurement in the Lyostar II software. These outputs were analyzed using JMP 9 software to evaluate the effect of the drying parameters on the second generation rFIXFc lyophilization process. A JMP stepwise analysis was performed to determine the significant variables, and these variables were then analyzed using a standard least squares effect screening algorithm which shows how the process outputs (residual moisture, product temperature and mass flow during drying) respond to the input variables.

Results and Discution

The results of the twelve lyophilization experiments are shown in Table 9.

TABLE 9

The DOE Results of Residual Moisture, Vial Mass Flow and Product Temperature

| Run | Temp (C.) | Vacuum (mT) | Time (hr) | NB Ref | % Moisture | dm/dt (g/hr/vial) | Tp (MTM, ° C.) |
| --- | --- | --- | --- | --- | --- | --- | --- |
| 1 | 40 | 100 | 35 | 16322-117 | 0.33 | 0.53 | −26.5 |
| 2 | 0 | 100 | 15 | 16322-110 | 2.82 | 0.28 | −32.2 |

TABLE 9-continued

The DOE Results of Residual Moisture,
Vial Mass Flow and Product Temperature

| Run | Temp (C.) | Vacuum (mT) | Time (hr) | NB Ref | % Moisture | dm/dt (g/hr/vial) | Tp (MTM, ° C.) |
|---|---|---|---|---|---|---|---|
| 3 | 40 | 1000 | 25 | 16322-090 | 0.57 | 0.45 | −15.2 |
| 4 | 20 | 100 | 28.2 | 16322-139 | 1.28 | 0.41 | −29.5 |
| 5 | 20 | 500 | 25 | 16322-098 | 1.58 | 0.57 | −20.3 |
| 6 | 0 | 100 | 25 | 16322-151 | 2.18 | 0.27 | −32.5 |
| 7 | 20 | 550 | 25 | 16322-146 | 1.49 | 0.56 | −19.7 |
| 8 | 40 | 250 | 15 | 18266-004 | 0.59 | 0.70 | −21.9 |
| 9 | 20 | 1000 | 15 | 16322-131 | 1.95 | 0.38 | −15.6 |
| 10 | 0 | 1000 | 35 | 16322-124 | 2.56 | 0.17 | −15.8 |
| 11 | 10 | 500 | 25 | 16322-104 | 2.01 | 0.35 | −21.8 |
| 12 | 40 | 500 | 25 | 16322-083 | 0.49 | 0.56 | −19.8 |

1. Analysis of Lyophilization Cycle Parameters on Residual Moisture

Figure 2:
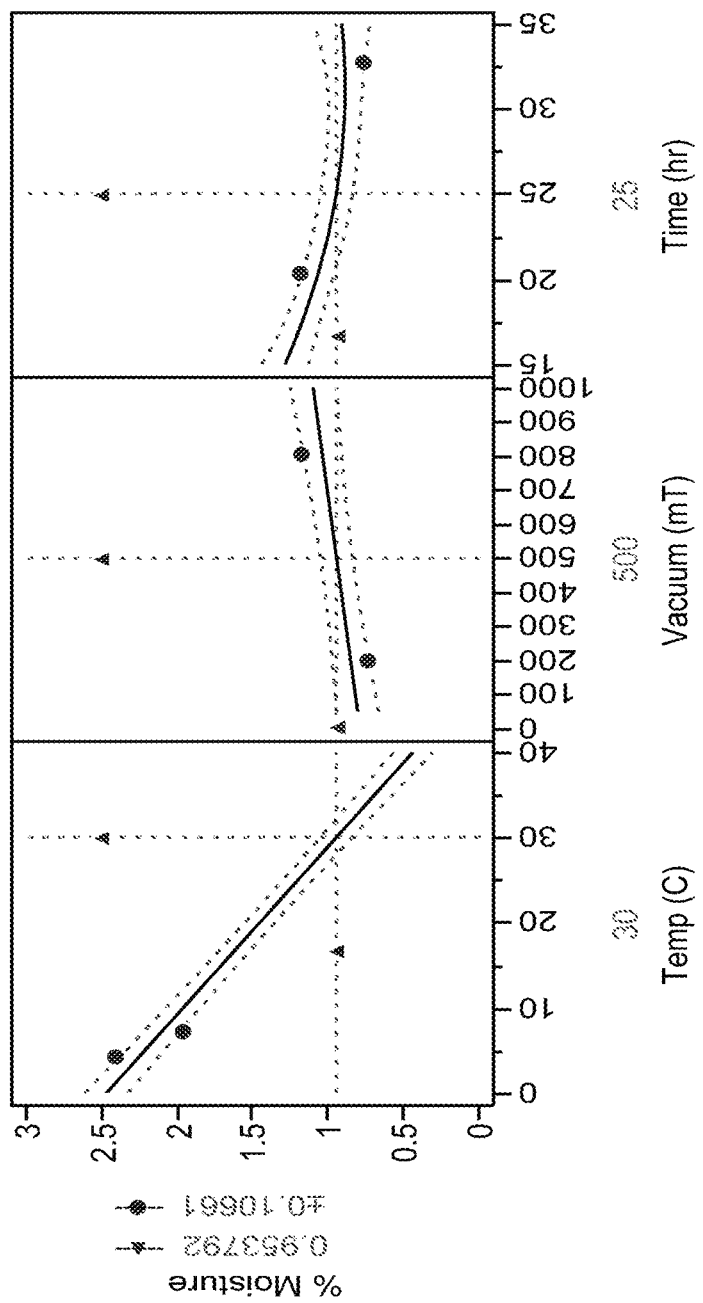
FIG. 2 shows the prediction profiler from the DOE analysis of residual moisture as a function of the lyophilization parameters—temperature, vacuum, and time.

The rFIXFc-2G placebo was used as a worst-case surrogate for the drug product as it is generally more difficult to remove residual moisture from sugars during secondary drying than protein. The resulting prediction profiler showing the outcome of the DOE analysis is shown in FIG. 2. Several observations are apparent: The shelf temperature has the most significant impact on the residual moisture in the drug product. This is expected based on the fact that secondary drying, which removes tightly bound water, is a diffusion and desorption controlled process. The model predicts with high confidence that shelf temperatures higher than 30° C. are required to achieve residual moisture levels lower than 1%. The vacuum level appears to have a small but measurable effect on the resulting residual moisture. The drying time appears to show a point of diminishing returns starting at 25 hours where the addition of further drying time does not continue to decrease the residual moisture level. This type of behavior is consistent with the kinetic approach to an equilibrium boundary determined by the shelf temperature, and the residual moisture approaches an asymptote where further drying is not possible. Based on this residual moisture DOE analysis the drying shelf temperature should be 30° C. or greater and the drying time should be fixed at 25 hours or less.

Figure 3:
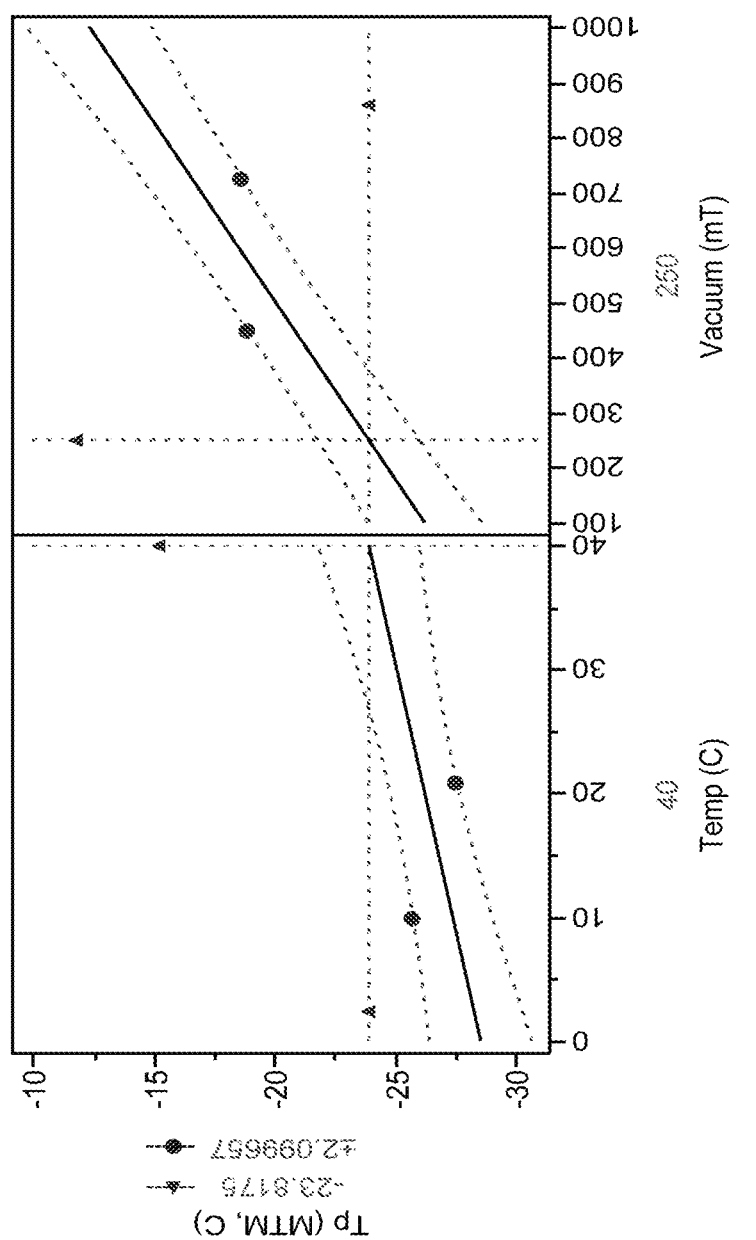
FIG. 3 shows the prediction profiler from the DOE analysis of product temperature during sublimation as a function of the lyophilization parameters—temperature and vacuum.

2. Analysis of Lyophilization Cycle Parameters on Product Temperature During Sublimation The freeze drying collapse temperature of the rFIXFc-2G Drug Product placebo has been measured as approximately −1.5° C. Practically, this means that the drug product will maintain an elegant cake structure so long as the product temperature is maintained below this collapse temperature as the bulk water is removed from the vial during lyophilization. The DOE analysis determined that the shelf temperature and chamber vacuum levels both had a significant effect on the product temperature as shown in FIG. 3. The chamber vacuum had the largest effect, with higher pressures translating to higher product temperatures during sublimation. Even at 1000 mTorr (1.33 mBar) the highest measured product temperature was −15.2° C., approximately 13° C. below the product collapse temperature. The shelf temperature also had a modest effect on the product temperature, but the results are less pronounced than the vacuum effect. This analysis shows that there is little risk of collapse even at a shelf temperature of 40° C. and a chamber vacuum level of 1000 mTorr, essentially eliminating the potential of collapse from any practical lyophilization cycle design space.

Figure 4:
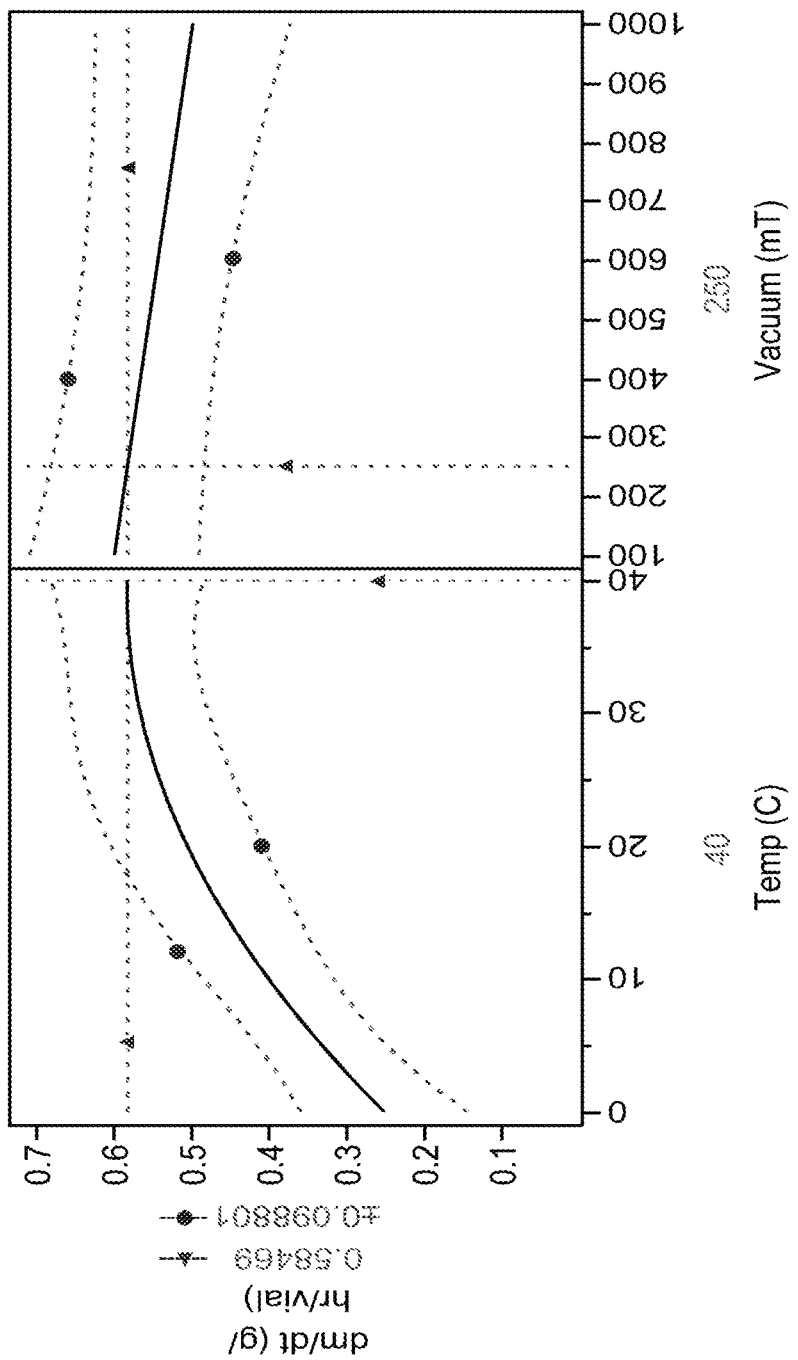
FIG. 4 shows the prediction profiler from the DOE analysis of vial mass flow during sublimation as a function of the lyophilization parameters—temperature and vacuum.

3. Analysis of Lyophilization Cycle Parameters on Vial Mass Flow Rate During Sublimation The vial mass flow rate (dm/dt) is a measure of the rate at which water is being removed from the vials during the sublimation process. While faster drying is desirable to reduce the time required for the lyophilization cycle, too much moisture can overwhelm the condensers in manufacturing scale freeze driers and lead to a loss of vacuum control in the product chamber. The placebo represents the worst case vial mass flow conditions. Since there is no protein present in the formulation, the solids percentage in the cake is minimized and this results in a lower resistance to mass flow from the freeze dried cake. The shelf temperature has a significant effect on the vial mass flow as shown in FIG. 4 with increasing temperature causing faster sublimation. The chamber vacuum level was included in the DOE analysis model, but the p value is 0.136 which is not significant with 95% confidence. The highest measured dm/dt in the study was 0.7 g/hr/vial.

Figure 5:
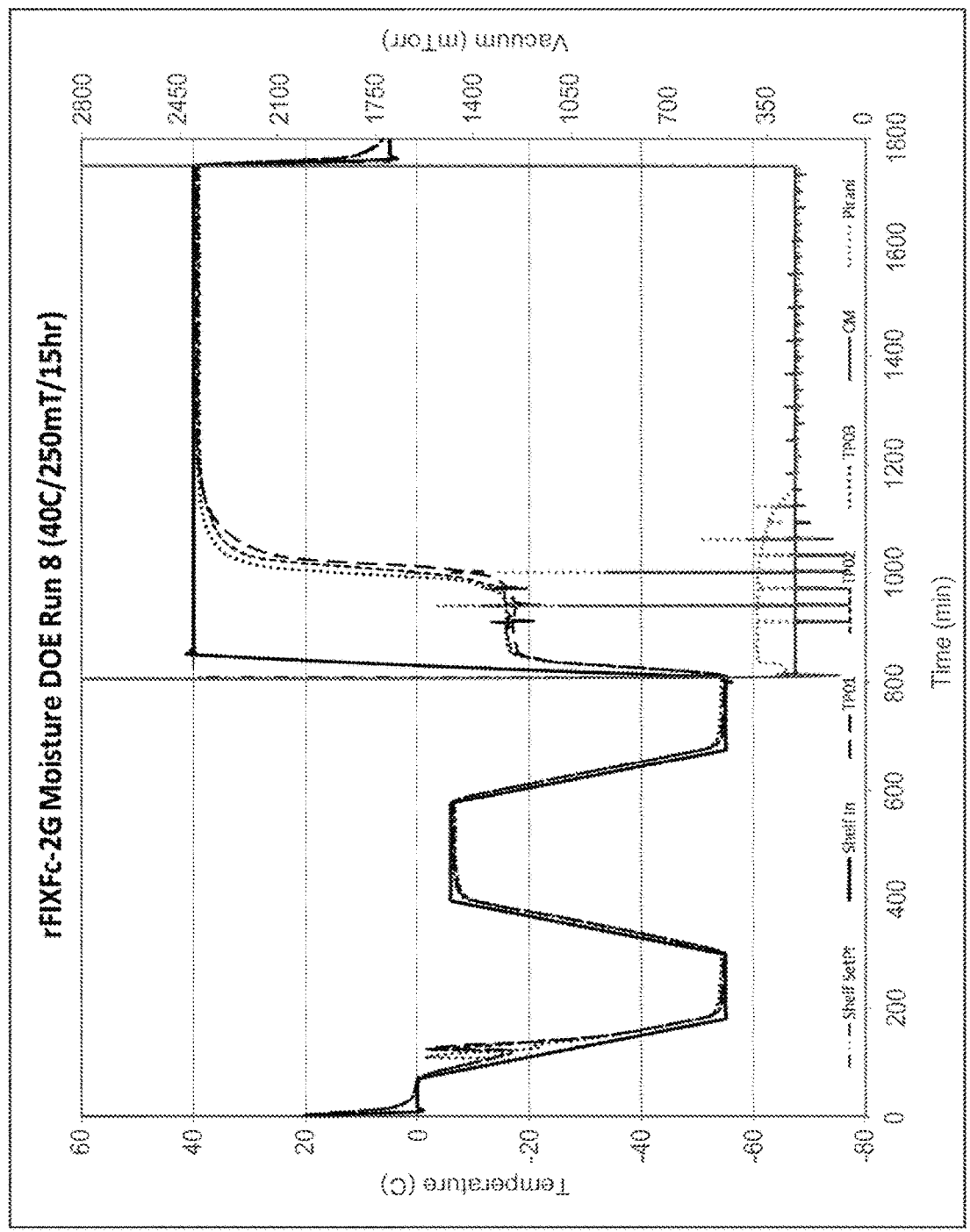
FIG. 5 shows the lyophilization data from DOE Run 8 in Example 2, which is similar to the proposed rFIXFc-2G lyophilization cycle (shelf temperature of 40° C., a chamber vacuum of 250 mTorr (0.33 mBar) and a drying time of 25 hours).

4. Proposed Second Generation rFIXFc Lyophilization Cycle Based on the Placebo DOE Study The data from the Placebo DOE study suggest it is feasible to design a lyophilization cycle to achieve a residual moisture target of <0.5% while maintaining the product below its collapse temperature using a single drying step. The proposed lyophilization cycle is shown in Table 10, and the data from DOE Run 8 which is under similar conditions to the proposed rFIXFc-2G lyophilization cycle is shown in FIG. 5. The residual moisture target of 0.5% was selected as this is the average value of the first generation rFIXFc drug product strength series. This moisture level provides a cushion so that as the product absorbs moisture during accelerated stability, product quality attributes will not be affected.

The freezing and annealing portions of the lyophilization cycle were used as developed for the reference rFIXFc drug product lyophilization cycle, and the separate primary and secondary drying steps have been replaced with a single drying step at 40° C. shelf temperature and 250 mTorr vacuum for 25 hours.

TABLE 10

The Proposed Lyophilization Cycle for rFIXFc-2G

| Phase | Step | Temp (° C.) | Ramp (° C./min) | Soak (min) | Vacuum (mTorr) |
|---|---|---|---|---|---|
| Load | Load | 25 | — | As Needed | — |
| Freeze | Equilibrate | 0 | 0.5 | 60 | — |
|  | Freeze | −55 | 0.5 | 120 | — |
|  | Anneal | −6 | 0.5 | 180 | — |
|  | Freeze | −55 | 0.5 | 120 | — |
| Pulldown | Initial Vac | −55 | — | — | 250 |
| Drying | 1°/2° Drying | 40 | 0.5 | 1500 | 250 |
| Final | Final | 5 | 5.0 | As Needed | 250 |

Conclusions

A 12 experiment DOE study evaluating the Second Generation rFIXFc Drug Product lyophilization process parameters on the residual moisture, product temperature and vial mass flow rate of the placebo was completed. An analysis of the data shows that in order to achieve a residual moisture level below 1%, a minimum shelf temperature of 30° C. during the drying phase is required. The analysis also demonstrated that drying times longer than 25 hours do not significantly decrease the residual moisture in the vials, and the vacuum level has only a small effect on the residual moisture. The product temperatures during drying are significantly affected by the shelf temperature and chamber vacuum level. The most aggressive conditions in the study (40° C. Shelf Temperature at 1000 mTorr Chamber Vacuum) resulted in a product temperature that was more than 10° C. colder than the collapse temperature.

A lyophilization cycle was proposed to achieve product with <0.5% residual moisture using a shelf temperature of 40° C., a chamber vacuum of 250 mTorr (0.33 mBar) and a drying time of 25 hours.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents. Other embodiments of the invention will be apparent to those skilled in the art from consideration of the specification and practice of the invention disclosed herein.

All documents, articles, publications, patents, and patent applications mentioned in this specification are herein incorporated by reference to the same extent as if each individual publication or patent application was specifically and individually indicated to be incorporated by reference.

The present application claims priority to U.S. Provisional Application No. 61/969,801, filed Mar. 24, 2014, which is incorporated herein by reference in its entirety.

TABLE OF SEQUENCES

TABLE 11

Polynucleotide Sequences of FIX
FIX-Fc Chain DNA Sequence (FIX signal peptide underlined,
FIX sequence double underlined, Fc region in bold)
(SEQ ID NO: 1, which encodes SEQ ID NO: 2)
pSYN-FIX-030 Nucleotide sequence (nt 1 to 7583):
FIX exon 1 (signal peptide, 1st amino acid propeptide):
nt 690-777
FIX mini intron: nt 778-1076
FIX sequence: nt 1077-2371
Fc: nt 2372-3052

```
   1 gcgcgcgttg acattgatta ttgactagtt attaatagta atcaattacg 51 gggtcattag ttcatagccc atatatggag ttccgcgtta cataacttac 101 ggtaaatggc ccgcctggct gaccgcccaa cgacccccgc ccattgacgt 151 caataatgac gtatgttccc atagtaacgc caatagggac tttccattga 201 cgtcaatggg tggagtattt acggtaaact gcccacttgg cagtacatca 251 agtgtatcat atgccaagta cgccccctat tgacgtcaat gacggtaaat 301 ggcccgcctg gcattatgcc cagtacatga ccttatggga ctttcctact 351 tggcagtaca tctacgtatt agtcatcgct attaccatgg tgatgcggtt 401 ttggcagtac atcaatgggc gtggatagcg gtttgactca cggggatttc 451 caagtctcca ccccattgac gtcaatggga gtttgttttg gcaccaaaat 501 caacgggact ttccaaaatg tcgtaacaac tccgccccat tgacgcaaat 551 gggcggtagg cgtgtacggt gggaggtcta tataagcaga gctctctggc 601 taactagaga acccactgct tactggctta tcgaaattaa tacgactcac 651 tatagggaga cccaagcttc gcgacgtacg gccgccacca tgcagcgcgt 701 gaacatgatc atggcagaat caccaggcct catcaccatc tgccttttag 751 gatatctact cagtgctgaa tgtacaggtt tgtttccttt tttaaaatac 801 attgagtatg cttgccttt agatatagaa atatctgatg ctgtcttctt 851 cactaaattt tgattacatg atttgacagc aatattgaag agtctaacag 901 ccagcacgca ggttggtaag tactgtggga acatcacaga ttttggctcc 951 atgccctaaa gagaaattgg ctttcagatt atttggatta aaaacaaaga 1001 ctttcttaag agatgtaaaa ttttcatgat gttttctttt ttgctaaaac
```

TABLE 11-continued

Polynucleotide Sequences of FIX
FIX-Fc Chain DNA Sequence (FIX signal peptide underlined,
FIX sequence double underlined, Fc region in bold)
(SEQ ID NO: 1, which encodes SEQ ID NO: 2)
pSYN-FIX-030 Nucleotide sequence (nt 1 to 7583):
FIX exon 1 (signal peptide, 1st amino acid propeptide):
nt 690-777
FIX mini intron: nt 778-1076
FIX sequence: nt 1077-2371
Fc: nt 2372-3052

```
1051 taaagaatta ttcttttaca tttcagtttt tcttgatcat gaaaacgcca 1101 acaaaattct gaatcggcca aagaggtata attcaggtaa attggaagag 1151 tttgttcaag ggaatctaga gagagaatgt atggaagaaa agtgtagttt 1201 tgaagaagca cgagaagttt ttgaaaacac tgaaagaaca actgaatttt 1251 ggaagcagta tgttgatgga gatcagtgtg agtccaatcc atgtttaaat 1301 ggcggcagtt gcaaggatga cattaattcc tatgaatgtt ggtgtccctt 1351 tggatttgaa ggaaagaact gtgaattaga tgtaacatgt aacattaaga 1401 atggcagatg cgagcagttt tgtaaaaata gtgctgataa caaggtggtt 1451 tgctcctgta ctgagggata tcgacttgca gaaaaccaga gtcctgtga 1501 accagcagtg ccatttccat gtggaagagt ttctgtttca caaacttcta 1551 agctcacccg tgctgagact gttttcctg atgtggacta tgtaaattct 1601 actgaagctg aaaccatttt ggataacatc actcaaagca cccaatcatt 1651 taatgacttc actcgggttg ttggtggaga agatgccaaa ccaggtcaat 1701 tcccttggca ggttgttttg aatggtaaag ttgatgcatt ctgtggaggc 1751 tctatcgtta atgaaaaatg gattgtaact gctgccact gtgttgaaac 1801 tggtgttaaa attacagttg tcgcaggtga acataatatt gaggagacag 1851 aacatacaga gcaaaagcga aatgtgattc gaattattcc tcaccacaac 1901 tacaatgcag ctattaataa gtacaaccat gacattgccc ttctggaact 1951 ggacgaaccc ttagtgctaa acagctacgt tacacctatt tgcattgctg 2001 acaaggaata cacgaacatc ttcctcaaat ttggatctgg ctatgtaagt 2051 ggctggggaa gagtcttcca caaagggaga tcagctttag ttcttcagta 2101 ccttagagtt ccacttgttg accgagccac atgtcttcga tctacaaagt 2151 tcaccatcta taacaacatg ttctgtgctg gcttccatga aggaggtaga 2201 gattcatgtc aaggagatag tggggaccc catgttactg aagtggaagg 2251 gaccagtttc ttaactggaa ttattagctg gggtgaagag tgtgcaatga 2301 aaggcaaata tggaatatat accaaggtgt cccggtatgt caactggatt 2351 aaggaaaaaa caaagctcac tgacaaaact cacacatgcc caccgtgccc 2401 agctccggaa ctcctgggcg gaccgtcagt cttcctcttc cccccaaaac 2451 ccaaggacac cctcatgatc tcccggaccc ctgaggtcac atgcgtggtg 2501 gtggacgtga gccacgaaga ccctgaggtc aagttcaact ggtacgtgga 2551 cggcgtggag gtgcataatg ccaagacaaa gccgcgggag gagcagtaca 2601 acagcacgta ccgtgtggtc agcgtcctca ccgtcctgca ccaggactgg 2651 ctgaatggca aggagtacaa gtgcaaggtc tccaacaaag ccctcccagc 2701 ccccatcgag aaaaccatct ccaaagccaa agggcagccc cgagaaccac 2751 aggtgtacac cctgccccca tcccgggatg agctgaccaa gaaccaggtc
```

TABLE 11-continued

Polynucleotide Sequences of FIX
FIX-Fc Chain DNA Sequence (FIX signal peptide underlined,
FIX sequence double underlined, Fc region in bold)
(SEQ ID NO: 1, which encodes SEQ ID NO: 2)
pSYN-FIX-030 Nucleotide sequence (nt 1 to 7583):
FIX exon 1 (signal peptide, 1st amino acid propeptide):
nt 690-777
FIX mini intron: nt 778-1076
FIX sequence: nt 1077-2371
Fc: nt 2372-3052

```
2801 agcctgacct gcctggtcaa aggcttctat cccagcgaca tcgccgtgga
2851 gtgggagagc aatgggcagc cggagaacaa ctacaagacc acgcctcccg
2901 tgttggactc cgacggctcc ttcttcctct acagcaagct caccgtggac
2951 aagagcaggt ggcagcaggg gaacgtcttc tcatgctccg tgatgcatga
3001 ggctctgcac aaccactaca cgcagaagag cctctccctg tctccgggta
3051 aatgagaatt cagacatgat aagatacatt gatgagtttg acaaaccac
3101 aactagaatg cagtgaaaaa aatgctttat ttgtgaaatt tgtgatgcta
3151 ttgctttatt tgtaaccatt ataagctgca ataaacaagt tggggtgggc
3201 gaagaactcc agcatgagat ccccgcgctg gaggatcatc cagccggcgt
3251 cccggaaaac gattccgaag cccaaccttt catagaaggc ggcggtggaa
3301 tcgaaatctc gtagcacgtg tcagtcctgc tcctcggcca cgaagtgcac
3351 gcagttgccg ccgggtcgc gcagggcgaa ctcccgcccc cacggctgct
3401 cgccgatctc ggtcatggcc ggcccggagg cgtcccggaa gttcgtggac
3451 acgacctccg accactcggc gtacagctcg tccaggccgc gcacccacac
3501 ccaggccagg gtgttgtccg gcaccacctg gtcctggacc gcgctgatga
3551 acagggtcac gtcgtcccgg accacaccgg cgaagtcgtc ctccacgaag
3601 tcccgggaga acccgagccg gtcggtccag aactcgaccg ctccggcgac
3651 gtcgcgcgcg gtgagcaccg gaacggcact ggtcaacttg gccatggttt
3701 agttcctcac cttgtcgtat tatactatgc cgatatacta tgccgatgat
3751 taattgtcaa cacgtgctga tcagatccga aaatggatat acaagctccc
3801 gggagctttt tgcaaaagcc taggcctcca aaaaagcctc ctcactactt
3851 ctggaatagc tcagaggcag aggcggcctc ggcctctgca taaataaaaa
3901 aaattagtca gccatgggc ggagaatggg cggaactggg cggagttagg
3951 ggcgggatgg gcggagttag gggcgggact atggttgctg actaattgag
4001 atgcatgctt tgcatacttc tgcctgctgg ggagcctggg gactttccac
4051 acctggttgc tgactaattg agatgcatgc tttgcatact tctgcctgct
4101 ggggagcctg gggactttcc acaccctcgt cgagctagct tcgtgaggct
4151 ccggtgcccg tcagtgggca gagcgcacat cgcccacagt ccccgagaag
4201 ttggggggag gggtcggcaa ttgaaccggt gcctagagaa ggtggcgcgg
4251 ggtaaactgg gaaagtgatg tcgtgtactg gctccgcctt tttcccgagg
4301 gtgggggaga accgtatata agtgcagtag tcgccgtgaa cgttcttttt
4351 cgcaacgggt ttgccgccag aacacaggta agtgccgtgt gtggttcccg
4401 cgggcctggc ctctttacgg gttatggcc ttgcgtgcct tgaattactt
4451 ccacctggct ccagtacgtg attcttgatc ccgagctgga gccaggggcg
```

TABLE 11-continued

Polynucleotide Sequences of FIX
FIX-Fc Chain DNA Sequence (FIX signal peptide underlined,
FIX sequence double underlined, Fc region in bold)
(SEQ ID NO: 1, which encodes SEQ ID NO: 2)
pSYN-FIX-030 Nucleotide sequence (nt 1 to 7583):
FIX exon 1 (signal peptide, 1st amino acid propeptide):
nt 690-777
FIX mini intron: nt 778-1076
FIX sequence: nt 1077-2371
Fc: nt 2372-3052

```
4501 ggccttgcgc tttaggagcc ccttcgcctc gtgcttgagt tgaggcctgg
4551 cctgggcgct ggggccgccg cgtgcgaatc tggtggcacc ttcgcgcctg
4601 tctcgctgct ttcgataagt ctctagccat ttaaaatttt tgatgacctg
4651 ctgcgacgct ttttttctgg caagatagtc ttgtaaatgc gggccaggat
4701 ctgcacactg gtatttcggt ttttggggcc gcgggcggcg acggggcccg
4751 tgcgtcccag cgcacatgtt cggcgaggcg gggcctgcga gcgcggccac
4801 cgagaatcgg acgggggtag tctcaagctg gccggcctgc tctggtgcct
4851 ggcctcgcgc cgccgtgtat cgccccgccc tgggcggcaa ggctggcccg
4901 gtcggcacca gttgcgtgag cggaaagatg ccgcttccc ggccctgctc
4951 caggggctc aaaatggagg acgcggcgct cgggagagcg ggcgggtgag
5001 tcacccacac aaaggaaagg ggcctttccg tcctcagccg tcgcttcatg
5051 tgactccacg gagtaccggg cgccgtccag gcacctcgat tagttctgga
5101 gcttttggag tacgtcgtct ttaggttggg gggaggggtt ttatgcgatg
5151 gagtttcccc acactgagtg ggtggagact gaagttaggc cagcttggca
5201 cttgatgtaa ttctccttgg aatttgcccc ttttgagttt ggatcttggt
5251 tcattctcaa gcctcagaca gtggttcaaa gtttttttct tccatttcag
5301 gtgtcgtgaa cacgtggtcg cggccgcgcc gccaccatgg agacagacac
5351 actcctgcta tgggtactgc tgctctgggt tccaggttcc actggtgaca
5401 aaactcacac atgcccaccg tgcccagcac ctgaactcct gggaggaccg
5451 tcagtcttcc tcttcccccc aaaacccaag gacaccctca tgatctcccg
5501 gacccctgag gtcacatgcg tggtggtgga cgtgagccac gaagaccctg
5551 aggtcaagtt caactggtac gtggacggcg tggaggtgca taatgccaag
5601 acaaagccgc gggaggagca gtacaacagc acgtaccgtg tggtcagcgt
5651 cctcaccgtc ctgcaccagg actggctgaa tggcaaggag tacaagtgca
5701 aggtctccaa caaagccctc ccagccccca tcgagaaaac catctccaaa
5751 gccaaagggc agccccgaga accacaggtg tacaccctgc ccccatcccg
5801 cgatgagctg accaagaacc aggtcagcct gacctgcctg gtcaaaggct
5851 tctatcccag cgacatcgcc gtggagtggg agagcaatgg gcagccggag
5901 aacaactaca agaccacgcc tcccgtgttg gactccgacg gctccttctt
5951 cctctacagc aagctcaccg tggacaagag caggtggcag caggggaacg
6001 tcttctcatg ctccgtgatg catgaggctc tgcacaacca ctacacgcag
6051 aagagcctct ccctgtctcc gggtaaatga ctcgagagat ctggccggct
6101 gggcccgttt cgaaggtaag cctatcccta accctctcct cggtctcgat
6151 tctacgcgta ccggtcatca tcaccatcac cattgagttt aaacccgctg
6201 atcagcctcg actgtgcctt ctagttgcca gccatctgtt gtttgcccct
```

TABLE 11-continued

Polynucleotide Sequences of FIX
FIX-Fc Chain DNA Sequence (FIX signal peptide underlined,
FIX sequence double underlined, Fc region in bold)
(SEQ ID NO: 1, which encodes SEQ ID NO: 2)
pSYN-FIX-030 Nucleotide sequence (nt 1 to 7583):
FIX exon 1 (signal peptide, 1st amino acid propeptide):
nt 690-777
FIX mini intron: nt 778-1076
FIX sequence: nt 1077-2371
Fc: nt 2372-3052

```
6251 cccccgtgcc ttccttgacc ctggaaggtg ccactcccac tgtcctttcc 6301 taataaaatg aggaaattgc atcgcattgt ctgagtaggt gtcattctat 6351 tctgggggt ggggtggggc aggacagcaa gggggaggat tgggaagaca 6401 atagcaggca tgctggggat gcggtgggct ctatggcttc tgaggcggaa 6451 agaaccagtg gcggtaatac ggttatccac agaatcaggg gataacgcag 6501 gaaagaacat gtgagcaaaa ggccagcaaa aggccaggaa ccgtaaaaag 6551 gccgcgttgc tggcgttttt ccataggctc cgcccccctg acgagcatca 6601 caaaaatcga cgctcaagtc agaggtggcg aaacccgaca ggactataaa 6651 gataccaggc gtttccccct agaagctccc tcgtgcgctc tcctgttccg 6701 accctgccgc ttaccggata cctgtccgcc tttctccctt cgggaagcgt 6751 ggcgctttct catagctcac gctgtaggta tctcagttcg gtgtaggtcg 6801 ttcgctccaa gctgggctgt gtgcacgaac cccccgttca gcccgaccgc 6851 tgcgccttat ccggtaacta tcgtcttgag tccaacccgg taagacacga 6901 cttatcgcca ctggcagcag ccactggtaa caggattagc agagcgaggt 6951 atgtaggcgg tgctacagag ttcttgaagt ggtggcctaa ctacggctac 7001 actagaagaa cagtatttgg tatctgcgct ctgctgaagc cagttacctt 7051 cggaaaaaga gttggtagct cttgatccgg caaacaaacc accgctggta 7101 gcggtggttt ttttgtttgc aagcagcaga ttacgcgcag aaaaaaagga 7151 tctcaagaag atcctttgat cttttctacg gggtctgacg ctcagtggaa 7201 cgaaaactca cgttaaggga ttttggtcat gacattaacc tataaaaata 7251 ggcgtatcac gaggcccttt cgtctcgcgc gtttcggtga tgacggtgaa 7301 aacctctgac acatgcagct cccggagacg gtcacagctt gtctgtaagc 7351 ggatgccggg agcagacaag cccgtcaggg cgcgtcagcg ggtgttggcg 7401 ggtgtcgggg ctggcttaac tatgcggcat cagagcagat tgtactgaga 7451 gtgcaccata tatgcggtgt gaaataccgc acagatgcgt aaggagaaaa 7501 taccgcatca ggcgccattc gccattcagg ctgcgcaact gttgggaagg 7551 gcgatcggtg cgggcctctt cgctattacg cca
```

TABLE 12

Polypeptide Sequences of FIX
FIX-Fc Monomer Hybrid: created by coexpressing
FIX-Fc and Fc chains.
A. FIX-Fc chain (SEQ ID NO: 2)
The c-terminal lysine is not present in either subunit;
this processing is often observed in recombinant proteins
produced in mammalian cell culture, as well as with
plasma derived proteins.
FIX-Fc-SC Subunit (the Fc part of FIX-Fc is in bold):

```
  1 YNSGKLEEFV QGNLERECME EKCSFEEARE VFENTERTTE FWKQYVDGDQ

51 CESNPCLNGG SCKDDINSYE CWCPFGFEGK NCELDVTCNI KNGRCEQFCK

101 NSADNKVVCS CTEGYRLAEN QKSCEPAVPF PCGRVSVSQT SKLTRAETVF

151 PDVDYVNSTE AETILDNITQ STQSFNDFTR VVGGEDAKPG QFPWQVVLNG

201 KVDAFCGGSI VNEKWIVTAA HCVETGVKIT VVAGEHNIEE TEHTEQKRNV

251 IRIIPHHNYN AAINKYNHDI ALLELDEPLV LNSYVTPICI ADKEYTNIFL

301 KFGSGYVSGW GRVFHKGRSA LVLQYLRVPL VDRATCLRST KFTIYNNMFC

351 AGFHEGGRDS CQGDSGGPHV TEVEGTSFLT GIISWGEECA MKGKYGIYTK

401 VSRYVNWIKE KTKLTDKTHT CPPCPAPELL GGPSVFLFPP KPKDTLMISR

451 TPEVTCVVVD VSHEDPEVKF NWYVDGVEVH NAKTKPREEQ YNSTYRVVSV

501 LTVLHQDWLN GKEYKCKVSN KALPAPIEKT ISKAKGQPRE PQVYTLPPSR

551 DELTKNQVSL TCLVKGFYPS DIAVEWESNG QPENNYKTTP PVLDSDGSFF

601 LYSKLTVDKS RWQQGNVFSC SVMHEALHNH YTQKSLSLSP GK
```

TABLE 13

Polynucleotide Sequences of Fc
Fc DNA sequence (mouse Igκ signal peptide underlined)
(SEQ ID NO: 3, which encodes SEQ ID NO: 4)

```
  1 atggagacag acacactcct gctatgggta ctgctgctct gggttccagg 51 ttccactggt gacaaaactc acacatgccc accgtgccca gcacctgaac 101 tcctggggagg accgtcagtc ttcctcttcc cccaaaaacc caaggacacc 151 ctcatgatct cccggacccc tgaggtcaca tgcgtggtgg tggacgtgag 201 ccacgaagac cctgaggtca agttcaactg gtacgtggac ggcgtggagg 251 tgcataatgc caagacaaag ccgcgggagg agcagtacaa cagcacgtac 301 cgtgtggtca gcgtcctcac cgtcctgcac caggactggc tgaatggcaa 351 ggagtacaag tgcaaggtct ccaacaaagc cctcccagcc cccatcgaga 401 aaaccatctc caaagccaaa gggcagcccc gagaaccaca ggtgtacacc 451 ctgccccat cccgcgatga gctgaccaag aaccaggtca gcctgacctg 501 cctggtcaaa ggcttctatc ccagcgacat cgccgtggag tgggagagca 551 atgggcagcc ggagaacaac tacaagacca cgcctcccgt gttggactcc 601 gacggctcct tcttcctcta cagcaagctc accgtggaca agagcaggtg 651 gcagcagggg aacgtcttct catgctccgt gatgcatgag gctctgcaca 701 accactacac gcagaagagc ctctccctgt ctccgggtaa a
```

TABLE 14

Polypeptide Sequences of Fc
Fc chain (SEQ ID NO: 4)

```
  1 DKTHTCPPCP APELLGGPSV FLFPPKPKDT LMISRTPEVT CVVVDVSHED

51 PEVKFNWYVD GVEVHNAKTK PREEQYNSTY RVVSVLTVLH QDWLNGKEYK

101 CKVSNKALPA PIEKTISKAK GQPREPQVYT LPPSRDELTK NQVSLTCLVK

151 GFYPSDIAVE WESNGQPENN YKTTPPVLDS DGSFFLYSKL TVDKSRWQQG

201 NVFSCSVMHE ALHNHYTQKS LSLSPGK
```

What is claimed is:

1. A pre-lyophilization formulation within a vial comprising:
   (a) a chimeric Factor IX (FIX) polypeptide, comprising FIX and a heterologous moiety that extends the half-life of the FIX, in an amount of about 2,000, about 3,000, or about 4,000 IU;
   (b) L-histidine at a concentration between 3 mg/ml and 15 mg/mL;
   (c) sucrose at a concentration between 10 mg/mL and 50 mg/mL;
   (d) mannitol at a concentration between 20 mg/mL and 100 mg/ml; and
   (e) polysorbate 20 at a concentration between 0.01 mg/ml and 5 mg/mL,
   wherein the formulation has a fill volume between 2 mL and 3 mL, and
   wherein the formulation is capable of being lyophilized into a lyophilate formulation having a residual moisture level below 2% using a lyophilization cycle with a cycle time of 4 days or less and a drying time of 25 hours or less.

2. The pre-lyophilization formulation of claim 1, wherein the fill volume is about 2.65 mL or about 2.5 mL.

3. The pre-lyophilization formulation of claim 1, wherein the L-histidine is at a concentration between about 5.82 mg/mL and about 9.7 mg/mL.

4. The pre-lyophilization formulation of claim 1, wherein the L-histidine is at a concentration of about 7.76 mg/mL.

5. The pre-lyophilization formulation of claim 1, wherein the sucrose is at a concentration between about 17.85 mg/mL and about 29.95 mg/mL.

6. The pre-lyophilization formulation of claim 1, wherein the sucrose is at a concentration of about 23.8 mg/mL.

7. The pre-lyophilization formulation of claim 1, wherein the mannitol is at a concentration between about 35.7 mg/mL and about 59.5 mg/mL.

8. The pre-lyophilization formulation of claim 1, wherein the mannitol is at a concentration of about 47.6 mg/mL.

9. The pre-lyophilization formulation of claim 1, wherein the polysorbate 20 is at a concentration between about 0.05 mg/mL and about 1 mg/mL.

10. The pre-lyophilization formulation of claim 1, wherein the polysorbate 20 is at a concentration of about 0.2 mg/mL.

11. The pre-lyophilization formulation of claim 1, wherein the chimeric FIX polypeptide is at a concentration between about 600 IU/mL and about 2,750 IU/mL.

12. A pre-lyophilization formulation within a vial comprising:
   (a) about 2,000, about 3,000, or about 4,000 IU of a chimeric Factor IX (FIX) polypeptide, comprising FIX and Fc;
   (b) about 7.76 mg/ml of L-histidine;
   (c) about 47.6 mg/mL of mannitol;
   (d) about 23.8 mg/ml of sucrose; and,
   (e) about 0.2 mg/ml of polysorbate 20;
   wherein the formulation has a fill volume between 2 mL and 3 mL, and
   wherein the formulation is capable of being lyophilized into a lyophilate formulation having a residual moisture level below 2% using a lyophilization cycle with a cycle time of 4 days or less and a drying time of 25 hours or less.

13. The pre-lyophilization formulation of claim 12, wherein the formulation has a fill volume per vial of about 2.65 mL or about 2.5 mL.

14. The pre-lyophilization formulation of claim 13, wherein the formulation has a fill volume per vial of about 2.65 mL.

15. The pre-lyophilization formulation of claim 1, wherein the moiety extending half-life of FIX comprises an FcRn binding partner or an Fc region.

16. The pre-lyophilization formulation of claim 1, wherein the chimeric FIX polypeptide comprises the FIXFc-sc polypeptide of SEQ ID NO: 2, without the C-terminal lysine, and the Fc sc polypeptide of SEQ ID NO:4, without the C-terminal lysine.

17. The pre-lyophilization formulation of claim 16, wherein the FIXFc-sc polypeptide and the Fc sc polypeptide are bound together through two disulfide bonds in the hinge region of Fc.

18. The pre-lyophilization formulation of claim 1, comprising 2,000 IU of the FIX polypeptide.

19. The pre-lyophilization formulation of claim 1, comprising 3,000 IU of the FIX polypeptide.

20. The pre-lyophilization formulation of claim 1, comprising 4,000 IU of the FIX polypeptide.

21. The pre-lyophilization formulation of claim 12, comprising 2,000 IU of the FIX polypeptide.

22. The pre-lyophilization formulation of claim 12, comprising 3,000 IU of the FIX polypeptide.

23. The pre-lyophilization formulation of claim 12, comprising 4,000 IU of the FIX polypeptide.

24. The pre-lyophilization formulation of claim 1, consisting essentially of:
 (a) about 2,000, about 3,000, or about 4,000 IU of a chimeric Factor IX (FIX) polypeptide, comprising FIX and a heterologous moiety that extends the half-life of the FIX;
 (b) L-histidine at a concentration between 3 mg/mL and 15 mg/mL;
 (c) sucrose at a concentration between 10 mg/ml and 50 mg/ml;
 (d) mannitol at a concentration between 20 mg/mL and 100 mg/mL; and
 (e) polysorbate 20 at a concentration between 0.01 mg/mL and 5 mg/mL,
 wherein the formulation has a fill volume between 2 mL and 3 mL.

25. The pre-lyophilization formulation of claim 24, consisting of:
 (a) about 2,000, about 3,000, or about 4,000 IU of a chimeric Factor IX (FIX) polypeptide, comprising FIX and a heterologous moiety that extends the half-life of the FIX;
 (b) L-histidine at a concentration between 3 mg/ml and 15 mg/ml;
 (c) sucrose at a concentration between 10 mg/mL and 50 mg/ml;
 (d) mannitol at a concentration between 20 mg/mL and 100 mg/mL; and
 (e) polysorbate 20 at a concentration between 0.01 mg/mL and 5 mg/mL,
 wherein the formulation has a fill volume between 2 mL and 3 mL.

26. The pre-lyophilization formulation of claim 1, wherein the formulation is capable of being lyophilized into a lyophilate formulation having a residual moisture level below 1% using a lyophilization cycle with a cycle time of 4 days or less and a drying time of 25 hours or less.

27. The pre-lyophilization formulation of claim 1, wherein the formulation is capable of being lyophilized into a lyophilate formulation having a residual moisture level below 0.5% using a lyophilization cycle with a cycle time of 4 days or less and a drying time of 25 hours or less.

28. The pre-lyophilization formulation of claim 12, wherein the formulation is capable of being lyophilized into a lyophilate formulation having a residual moisture level below 1% using a lyophilization cycle with a cycle time of 4 days or less and a drying time of 25 hours or less.

29. The pre-lyophilization formulation of claim 12, wherein the formulation is capable of being lyophilized into a lyophilate formulation having a residual moisture level below 0.5% using a lyophilization cycle with a cycle time of 4 days or less and a drying time of 25 hours or less.

30. The pre-lyophilization formulation of claim 24, comprising 2,000 IU of the chimeric FIX polypeptide.

31. The pre-lyophilization formulation of claim 24, comprising 3,000 IU of the chimeric FIX polypeptide.

32. The pre-lyophilization formulation of claim 24, comprising 4,000 IU of the chimeric FIX polypeptide.

33. The pre-lyophilization formulation of claim 25, comprising 2,000 IU of the chimeric FIX polypeptide.

34. The pre-lyophilization formulation of claim 25, comprising 3,000 IU of the chimeric FIX polypeptide.

35. The pre-lyophilization formulation of claim 25, comprising 4,000 IU of the chimeric FIX polypeptide.

36. The pre-lyophilization formulation of claim 1, wherein the lyophilization cycle comprises freezing the formulation in a vial and then ramping up the temperature in the vial to a drying temperature before the drying time of 25 hours or less, wherein the drying temperature is about 40° C.

* * * * *